US007250095B2

(12) United States Patent
Black et al.

(10) Patent No.: US 7,250,095 B2
(45) Date of Patent: Jul. 31, 2007

(54) ENZYME ELECTRODES AND METHOD OF MANUFACTURE

(75) Inventors: Murdo M. Black, Angus (GB); Colin Butters, Ipswich (GB); Wah O. Ho, Ipswich (GB); John Rippeth, Ipswich (GB)

(73) Assignee: Hypoguard Limited (GB)

( * ) Notice: Subject to any disclaimer, the term of this patent is extended or adjusted under 35 U.S.C. 154(b) by 713 days.

(21) Appl. No.: 10/617,262

(22) Filed: Jul. 10, 2003

(65) Prior Publication Data

US 2004/0061841 A1    Apr. 1, 2004

Related U.S. Application Data

(60) Provisional application No. 60/397,345, filed on Jul. 19, 2002.

(30) Foreign Application Priority Data

Jul. 11, 2002    (GB)    ................... 0216039.8

(51) Int. Cl.
*G01N 27/327*    (2006.01)
(52) U.S. Cl. ................ 204/403.14; 204/403.04; 204/403.11
(58) Field of Classification Search ........... 204/403.01–403.15; 205/777.5, 778
See application file for complete search history.

(56) References Cited

U.S. PATENT DOCUMENTS

| | | | |
|---|---|---|---|
| 3,836,033 A | 9/1974 | Mindt et al. | |
| 3,838,033 A | 9/1974 | Mindt et al. | |
| 3,979,274 A | 9/1976 | Newman | |
| 3,992,158 A | 11/1976 | Przybylowicz et al. | |
| 3,993,451 A | 11/1976 | Verbeck | |
| 4,053,381 A | 10/1977 | Hamblen et al. | |
| 4,137,495 A | 1/1979 | Brown | |
| 4,142,863 A | 3/1979 | Covington et al. | |
| 4,190,420 A | 2/1980 | Covington et al. | |
| 4,216,245 A | 8/1980 | Johnson | |
| 4,225,410 A | 9/1980 | Pace | |
| 4,233,029 A | 11/1980 | Columbus | |

(Continued)

FOREIGN PATENT DOCUMENTS

DE    19639226 A1    9/1996

(Continued)

OTHER PUBLICATIONS

Copending U.S. Appl. No. 11/028,942, filed Jan. 4, 2005, entitled "Biosensor And Method Of Manufacture" (DUMM:019).

(Continued)

*Primary Examiner*—Alex Noguerola
(74) *Attorney, Agent, or Firm*—O'Keefe, Egan, Peterman & Enders, LLP

(57)    ABSTRACT

A non-mediated enzyme electrode comprises a base substrate (2) on which is provided an electrically conductive base layer (8) comprising finely divided platinum group metal or oxide bonded together by a resin; a top layer on the base layer (8), the top layer comprising a buffer. A catalytically active quantity of an oxidoreductase enzyme is provided in at least one of the base layer and the top layer. The invention also provides a biosensor (20) which includes an enzyme electrode, and methods of manufacturing the enzyme electrode and biosensor.

43 Claims, 18 Drawing Sheets

U.S. PATENT DOCUMENTS

| | | | |
|---|---|---|---|
| 4,273,639 A | 6/1981 | Gottermeier | |
| 4,301,412 A | 11/1981 | Hill et al. | |
| 4,301,414 A | 11/1981 | Hill et al. | |
| 4,303,887 A | 12/1981 | Hill et al. | |
| 4,312,834 A | 1/1982 | Vogel et al. | |
| 4,413,407 A | 11/1983 | Columbus | |
| 4,418,148 A | 11/1983 | Oberhardt | |
| 4,473,457 A | 9/1984 | Columbus | |
| 4,476,149 A | 10/1984 | Poppe et al. | |
| 4,490,216 A | 12/1984 | McConnell | |
| 4,502,938 A | 3/1985 | Covington et al. | |
| 4,545,382 A | 10/1985 | Higgins et al. | |
| 4,591,550 A | 5/1986 | Hafeman et al. | |
| 4,637,978 A | 1/1987 | Dappen | |
| 4,654,127 A | 3/1987 | Baker et al. | |
| 4,654,197 A | 3/1987 | Lilja et al. | |
| 4,713,327 A | 12/1987 | Findlay et al. | |
| 4,714,874 A | 12/1987 | Morris et al. | |
| 4,849,623 A | 7/1989 | Osaki et al. | |
| 4,897,173 A | 1/1990 | Nankai et al. | |
| 4,900,405 A | 2/1990 | Otagawa et al. | |
| 4,970,145 A | 11/1990 | Bennetto et al. | |
| 4,978,503 A | 12/1990 | Shanks et al. | |
| 5,108,564 A | 4/1992 | Szuminsky et al. | |
| 5,118,404 A | 6/1992 | Saito | |
| 5,120,420 A | 6/1992 | Nankai et al. | |
| 5,128,015 A | 7/1992 | Szuminsky et al. | |
| 5,141,868 A | 8/1992 | Shanks et al. | |
| 5,160,278 A | 11/1992 | Johnson | |
| 5,160,418 A | 11/1992 | Mullen | |
| 5,185,256 A | 2/1993 | Nankai et al. | |
| 5,228,972 A | 7/1993 | Osaka et al. | |
| 5,231,028 A | 7/1993 | Mullen | |
| 5,232,668 A | 8/1993 | Grant et al. | |
| 5,271,896 A | 12/1993 | Jakubowicz et al. | |
| 5,281,395 A | 1/1994 | Markart et al. | |
| 5,288,636 A | 2/1994 | Pollmann et al. | |
| 5,335,816 A | 8/1994 | Kaufman et al. | |
| 5,335,822 A | 8/1994 | Kasper | |
| 5,366,609 A | 11/1994 | White et al. | |
| 5,395,504 A | 3/1995 | Saurer et al. | |
| 5,407,554 A | 4/1995 | Saurer | |
| 5,413,690 A | 5/1995 | Kost et al. | |
| 5,429,735 A | 7/1995 | Johnson et al. | |
| 5,508,171 A | 4/1996 | Walling et al. | |
| 5,509,410 A | 4/1996 | Hill et al. | |
| 5,525,297 A | 6/1996 | Dinger et al. | |
| 5,526,120 A | 6/1996 | Jina et al. | |
| 5,575,895 A * | 11/1996 | Ikeda et al. | 204/403.1 |
| 5,616,222 A | 4/1997 | Maley et al. | 204/294 |
| 5,628,890 A | 5/1997 | Carter et al. | |
| 5,660,791 A | 8/1997 | Brenneman et al. | |
| 5,682,884 A | 11/1997 | Hill et al. | |
| 5,708,247 A | 1/1998 | McAleer et al. | |
| 5,727,548 A | 3/1998 | Hill et al. | |
| 5,759,010 A | 6/1998 | Jacobs et al. | |
| 5,770,028 A | 6/1998 | Maley et al. | |
| 5,797,693 A | 8/1998 | Jaeger | |
| 5,820,551 A | 10/1998 | Hills et al. | |
| 5,985,116 A | 11/1999 | Ikeda et al. | |
| 5,989,917 A | 11/1999 | McAleer et al. | |
| 6,042,751 A | 3/2000 | Chan et al. | |
| 6,168,957 B1 | 1/2001 | Matzinger et al. | |
| 6,241,862 B1 | 6/2001 | McAleer et al. | |
| 6,248,596 B1 | 6/2001 | Durst et al. | |
| 6,258,229 B1 | 7/2001 | Winarata et al. | |
| 6,287,451 B1 | 9/2001 | Winarata et al. | |
| 6,338,790 B1 | 1/2002 | Feldman et al. | |
| 6,436,256 B1 | 8/2002 | Williams et al. | |
| 6,541,216 B1 | 4/2003 | Wilsey et al. | |
| 6,565,738 B1 * | 5/2003 | Henning et al. | 205/777.5 |
| 6,627,058 B1 * | 9/2003 | Chan | 204/403.15 |
| 6,656,702 B1 * | 12/2003 | Yugawa et al. | 435/26 |
| 6,863,800 B2 * | 3/2005 | Karinka et al. | 205/777.5 |
| 2002/0057993 A1 | 5/2002 | Maisey et al. | |
| 2002/0146835 A1 | 10/2002 | Modzelewski et al. | |
| 2003/0116583 A1 | 6/2003 | Pugh | |
| 2004/0178216 A1 | 9/2004 | Brickwood et al. | |
| 2005/0281706 A1 | 12/2005 | Funke et al. | |

FOREIGN PATENT DOCUMENTS

| | | |
|---|---|---|
| EP | 0010456 A1 | 4/1980 |
| EP | 0016387 A1 | 10/1980 |
| EP | 0034049 A1 | 8/1981 |
| EP | 0057110 A2 | 8/1982 |
| EP | 0078636 A1 | 5/1983 |
| EP | 0095946 A1 | 12/1983 |
| EP | 0096095 A1 | 12/1983 |
| EP | 0121385 A1 | 10/1984 |
| EP | 0127958 | 12/1984 |
| EP | 0136362 A1 | 4/1985 |
| EP | 0171148 A1 | 2/1986 |
| EP | 0186286 A1 | 7/1986 |
| EP | 0200539 B1 | 11/1986 |
| EP | 0212314 A2 | 3/1987 |
| EP | 0215446 A2 | 3/1987 |
| EP | 0225061 A1 | 6/1987 |
| EP | 0230472 A1 | 8/1987 |
| EP | 0239222 A1 | 9/1987 |
| EP | 0255291 A1 | 2/1988 |
| EP | 0267724 A1 | 5/1988 |
| EP | 0271102 A2 | 6/1988 |
| EP | 0359831 A1 | 3/1990 |
| EP | 0170375 B1 | 5/1990 |
| EP | 0373413 A1 | 6/1990 |
| EP | 0375363 A2 | 6/1990 |
| EP | 0115873 B1 | 11/1990 |
| EP | 0471986 A2 | 2/1992 |
| EP | 0127958 B1 | 3/1992 |
| EP | 0593096 A2 | 4/1994 |
| EP | 0636879 A2 | 2/1995 |
| EP | 0645627 A1 | 3/1995 |
| EP | 0732590 A3 | 1/1996 |
| EP | 0738666 B1 | 4/1996 |
| EP | 0732590 A2 | 9/1996 |
| EP | 0738666 A2 | 10/1996 |
| EP | 0771867 A2 | 5/1997 |
| EP | 0811843 A2 | 6/1997 |
| EP | 0885591 A2 | 12/1998 |
| EP | 0969097 A2 | 1/2000 |
| GB | 1318815 | 5/1973 |
| GB | 2001443 A | 1/1979 |
| GB | 2090659 A | 7/1982 |
| GB | 2227010 A | 7/1990 |
| GB | 2307231 A | 5/1997 |
| GB | 2337122 A | 11/1999 |
| GB | 2351153 A | 12/2000 |
| JP | 56163447 A | 12/1981 |
| JP | 59-40145 | 3/1984 |
| JP | 62030962 A | 2/1987 |
| JP | 62-237348 | 10/1987 |
| JP | 63-3248 | 1/1988 |
| JP | S61-146392 | 1/1988 |
| JP | 63-58149 | 3/1988 |
| JP | 63-137559 | 6/1988 |
| JP | 63-144245 | 6/1988 |
| JP | 63-144246 | 6/1988 |
| JP | 63-144247 | 6/1988 |
| JP | 63-317096 | 12/1988 |
| JP | 64-23152 | 1/1989 |
| JP | 64-23153 | 1/1989 |
| JP | 64-23154 | 1/1989 |
| JP | 1-14746 | 5/1989 |

| | | |
|---|---|---|
| JP | 1-114747 | 5/1989 |
| JP | 1-134242 | 5/1989 |
| JP | 1-134243 | 5/1989 |
| JP | 1-134244 | 5/1989 |
| JP | 1-212345 | 8/1989 |
| JP | 01253648 A * | 10/1989 |
| JP | 01291153 A * | 11/1989 |
| JP | 02062952 A * | 3/1990 |
| JP | 04326054 | 11/1992 |
| JP | 11344460 A | 12/1999 |
| WO | WO 88/03270 | 5/1988 |
| WO | WO 89/08713 | 9/1989 |
| WO | WO 92/14836 | 9/1992 |
| WO | WO9215861 A1 | 9/1992 |
| WO | WO94/10558 | 11/1993 |
| WO | WO9607907 A1 | 3/1996 |
| WO | WO 97/30344 | 8/1997 |
| WO | WO 98/19159 | 5/1998 |
| WO | WO98/55856 | 12/1998 |
| WO | WO 99/05966 | 2/1999 |
| WO | WO99/13100 | 3/1999 |
| WO | WO 01/23885 A1 | 8/1999 |
| WO | WO00/78992 | 12/2000 |
| WO | WO01/46457 A2 | 6/2001 |
| WO | WO 02/08753 A2 | 1/2002 |
| WO | WO 02/18940 A2 | 3/2002 |
| WO | WO02/057766 A2 | 7/2002 |
| WO | WO03/042691 A1 | 5/2003 |
| WO | WO2004/008130 A1 | 1/2004 |

OTHER PUBLICATIONS

Copending U.S. Appl. No. 11/028,941, filed Jan. 4, 2005, entitled "Biosensor And Method Of Manufacture" (DUMM:020).

Published PCT application WO 01/23855A1 corresponding to copending U.S. Appl. No. 10/089,048, filed Mar. 25, 2002, "Test Device".

Copending U.S. Appl. No. 10/094,501, filed Mar. 8, 2002, "Test Member Orientation".

Copending U.S. Appl. No. 10/233,265, filed Aug. 30, 2002, "Sensor Dispensing Device".

Copending U.S. Appl. No. 10/089,048, filed Mar. 25, 2002, "Test Device".

Copending U.S. Appl. No. 10/265,087, filed Oct. 4, 2002, "Test Meter Calibration".

Karl Schugerl et al., "Online-ProzeBanalyse In Bioreaktoren", No. 9, Germany, Sep. 1987.

International Search Report, PCT/GB03/02901; 3 pages.

* cited by examiner

FIG. 10 Effect of buffer type on H2O2 response

ENZYME ELECTRODES AND METHOD OF MANUFACTURE

This application claims priority to co-pending U.S. provisional application Ser. No. 60/397,345 filed on Jul. 19, 2002, which is entitled "ENZYME ELECTRODES AND METHOD OF MANUFACTURE," the disclosure of which is incorporated herein by reference. This application also claims priority to United Kingdom patent application serial number 0216039.8 filed Jul. 11, 2002, the disclosure of which is also incorporated herein by reference.

BACKGROUND OF THE INVENTION

1. Field of the Invention

The present invention relates to enzyme electrodes for measuring analyte concentration in fluids, for example glucose in whole blood. Enzyme electrodes comprise an enzyme layered on or mixed with an electrically conductive substrate. The electrodes respond amperometrically to the catalytic activity of the enzyme in the presence of a suitable analyte (substrate). The invention also extends to a biosensor, notably a single-use biosensor, which includes the enzyme electrode.

2. Description of the Prior Art

Amperometric biosensors are well known in the art. Typically the enzyme is an oxidoreductase, for example glucose oxidase, cholesterol oxidase, or lactate oxidase, which produces hydrogen peroxide according to the reaction:

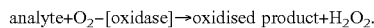

analyte+$O_2$-[oxidase]→oxidised product+$H_2O_2$.

The peroxide is oxidised at a fixed-potential electrode as follows:

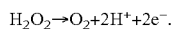

$H_2O_2 \rightarrow O_2 + 2H^+ + 2e^-$.

Electrochemical oxidation of hydrogen peroxide at the platinum centres on the electrode results in transfer of electrons from the peroxide to the electrode producing a current which is proportional to the analyte concentration. Where glucose is the analyte, the oxidised product is gluconolactone. Japanese Unexamined Patent Publication No. 56-163447 describes a system which employs glucose oxidase immobilised on a platinum electrode. The electrode comprises a layer of immobilised enzyme on an electrically conductive carbon base. The base is formed from moulded graphite containing up to 10 parts by weight of a fluorocarbon resin binder, onto which is deposited a thin (less than 1 μm) platinum film. The invention is said to avoid the problems associated with the immobilisation of the enzyme directly onto the platinum surface and to produce an enzyme electrode having rapid response times (5 seconds), high sensitivity and durability. However, according to U.S. Pat. No. 4,970,145, recent experimental work with such electrodes has failed to elicit such benefits.

U.S. Pat. No. 4,970,145 describes an enzyme electrode comprising a substantially heterogeneous porous substrate consisting essentially of resin-bonded carbon or graphite particles with a platinum-group metal dispersed substantially uniformly throughout the substrate, and a catalytically active quantity of an enzyme adsorbed or immobilised onto the surfaces of the porous substrate. The electrodes are manufactured either by cross-linking the enzyme to the substrate, or by suspending the porous substrate in a buffered solution of the enzyme for 90 minutes at room temperature. Alternatively, adsorption of the enzyme to the electrode is effected by electroadsorption, wherein the electrode base material is suspended at a positive potential in an enzyme solution for 60 minutes. The electrode is said to have fast response times (1-2 seconds without a protective membrane, and 10 to 30 seconds with a membrane) and good stability. The working range is said to be extended, and the electrode requires a substantially lower operating potential than normal (325 mV against the more usual 650 mV) and exhibits low background at the operating potential.

U.S. Pat. No. 5,160,418 discloses a simplified enzyme electrode comprising a thin film of a substantially homogeneous blend of enzyme and finely-divided platinum group metal or oxide. Optionally, platinised or palladised finely-divided carbon or graphite may be used and, also optionally, a binder. The film can be made by screen-printing a liquid suspension containing the components.

We have found that prior art systems such as described above have high intercepts relative to sensitivity, resulting in poor calibrated precision. We have also found that there is a gradual attenuation of sensitivity with time which is not necessarily related to enzyme instability.

As an alternative to measurement of an electrical signal following transfer of electrons from peroxide to the electrode, some biosensors include an electron carrier, or "mediator" which, in an oxidised form, accepts electrons from the enzyme and then, in a reduced state, transports the electrons to the electrode where it becomes re-oxidised. Prior art examples of mediators include ferrocene, ferrocene derivatives, ferricyanide, osmium complexes, 2,6-dichlorophenolindophenol, Nile Blue, and Medola Blue; see, for example: U.S. Pat. Nos. 5,708,247, 6,241,862, WO 98/55856, and WO 99/13100. Biosensors that employ a redox mediator to transfer electrons between the enzyme and the electrode will be referred to as "mediated biosensors".

Mediated biosensors can suffer from a number of problems, including chemical instability. The mediator must be in a particular redox state to function, so that if the reduced form is oxidised by air the measured current will be reduced. Oxygen may also interfere by accepting electrons to form peroxides which are not oxidised at the potential of the mediated electrode. If the electrode potential is increased to oxidise the peroxide, this makes the system prone to interference from other species which may be dissolved in blood, for example paracetamol, ascorbate, and uric acid. Thus, variation in oxygen concentration in blood may cause variation in measured glucose response in a mediated system.

Desirable attributes for a single use biosensor include:
low intercept, related to background—to achieve low coefficients of variation (CV's) after calibration;
as high a sensitivity as the electronics will allow;
stability;
good precision;
reproducible manufacture;
rapid response;
low cost.

The present invention seeks to provide an enzyme electrode and biosensor which are improved in respect of at least some of the above criteria.

SUMMARY OF THE INVENTION

According to an aspect of the present invention there is provided a non-mediated enzyme electrode for indicating amperometrically the catalytic activity of an oxidoreductase enzyme in the presence of a fluid containing a substance acted upon by said enzyme and of an electric potential on the electrode, said electrode comprising a base substrate on which is provided:

(a) an electrically conductive base layer comprising finely divided platinum group metal or oxide bonded together by a resin;
(b) a top layer on the base layer, said top layer comprising a buffer; and
(c) a catalytically active quantity of said oxidoreductase enzyme in at least one of said base layer and said top layer.

The term "non-mediated" is used herein to refer to an enzyme electrode which does not contain any significant quantity of a redox mediator, and to a biosensor including such an enzyme electrode. Preferably, the enzyme electrode does not contain any redox mediator. Thus, when an oxidoreductase enzyme such as glucose oxidase is employed, all or substantially all of the measured current results from oxidation of peroxide at the electrode.

We have found that by providing the buffer in the top layer, we can get faster response times than conventional non-mediated biosensors, together with increased stability and sensitivity. The increase in sensitivity and response time we believe is achieved by providing a high buffering capacity on the strip. The oxidation of hydrogen peroxide produces hydrogen ions which are neutralised by the buffer. This can have two effects: it sustains enzyme activity by maintaining the local pH around the enzyme, and it also shifts the equilibrium of the hydrogen peroxide oxidation making it more efficient. Improving the efficiency of hydrogen peroxide oxidation also results in greater oxygen recycling which can be utilised by the oxidoreductase enzyme. We have also found that the ratio of enzyme to buffer is important in obtaining a desirable linearity of response and to obtain a reasonable lower limit of sensitivity. We have further found that the buffer and enzyme needs to exceed a particular threshold concentration to attain the maximum sensitivity and above this concentration the ratio of buffer to enzyme can be used to "tune" the profile of the response of the biosensor to blood glucose, as will be discussed later in the context of our experimental results.

The pH range for the buffer will depend on the specific chemistry of the system. A preferred range is pH 7-10, notably 7 to 8.5. Preferred buffers are phosphate, at about pH 8, and ADA at about pH 7.5.

The platinum group metal or oxide may be present in sufficient quantity for the base layer to be electrically conductive, as taught in U.S. Pat. No. 5,160,418. Alternatively, the base layer may also contain particles of finely divided carbon or graphite. For convenience, the term "catalyst" will be used herein to refer to the finely divided platinum group metal or oxide. In a preferred embodiment, the catalyst is in intimate surface contact with the carbon or graphite particles, for example as platinised carbon or palladised carbon.

The resin may comprise any compatible binder material or bonding agent which serves to bond the platinum group metal or oxide in the base layer; for example, a polyester resin, ethyl cellulose or ethylhydroxyethylcellulose (EHEC).

The enzyme electrode may be manufactured by printing an ink containing the catalyst on the base substrate, allowing the printed ink to dry to form a base layer, and subsequently forming the top layer by applying a coating medium comprising or containing the buffer. The coating medium is preferably a fluid, notably an aqueous fluid in which the buffer is dissolved. However, the coating medium could comprise a dry powder consisting of or containing the buffer, which is applied, for example by spraying, to a tacky base layer. Suitable methods for forming the top layer when a coating fluid is applied include printing, spraying, ink jet printing, dip-coating or spin coating. A preferred coating technique is drop coating of a coating fluid, and the invention will be described hereinafter with reference to this preferred method.

Typically, the enzyme electrode will be incorporated in the working electrode of a biosensor, and a reference electrode will also be provided for completing a circuit and providing a stable reference potential, as is well known in the art.

Accordingly, a further aspect of the invention provides a non-mediated biosensor for indicating amperometrically the catalytic activity of an oxidoreductase enzyme in the presence of a fluid containing a substance acted upon by said enzyme, the biosensor comprising:

(a) a base substrate;
(b) a working electrode and a reference electrode on the base substrate;
(c) conductive tracks connected to the said electrodes for making electrical connections with a test meter apparatus;

wherein the working electrode includes:

(d) an electrically conductive base layer comprising finely divided platinum group metal or oxide bonded together by a resin;
(e) a top layer on the base layer, said top layer comprising a buffer; and
(f) a catalytically active quantity of said oxidoreductase enzyme in at least one of said base layer and said top layer.

In a preferred embodiment, the enzyme is provided in the top layer with the buffer. This arrangement facilitates adjustment of the pH in the local environment of the top layer to a level at which the enzyme may operate more efficiently, which level is typically different from that at which the platinum group metal or oxide optimally operates.

A system stabiliser may advantageously be included in the top layer. Suitable stabilisers include polyols other than those which are acted upon by the enzyme; for example trehalose, mannitol, lactitol, sorbitol or sucrose where the enzyme is glucose oxidase. The system stabiliser may stabilise the enzyme by encapsulation, hindering tertiary structural changes on storage, or by replacing the water activity around the enzyme molecule. The glucose oxidase enzyme has been shown to be a very stable enzyme and the addition of stabilisers are not primarily to protect this enzyme. The stabilisers help to reduce long term catalyst passivation effects, for example by coating a platinised carbon resin base layer as well as blocking the carbon surface to air oxidation.

If carbon particles are present in the base layer, a blocking agent may optionally be included in that layer to block active sites on the carbon particles. This aids shelf stability and uniformity of the carbon's activity. Suitable blocking agents include the system stabilisers and also proteins, for example bovine serum albumin (BSA). If graphite particles are used instead of high surface carbon, the particles have higher conductivity, and a blocking agent is less desirable because the number of active moieties on the graphite is much less than that found on carbon. The smaller surface area and less active surface groups both tend to reduce the intercept. At 0 mM of analyte the intercept consists mainly of a capacitative component which is surface area related.

The base substrate may be formed from any suitably heat-stable material. Heat stability is important to ensure good registration of prints in the manufacturing process. A preferred substrate is Valox FR-1 thermoplastic polyester film (poly(butylene terephthalate) copoly (bisphenol-A/tertabromobisphenol-A-carbonate). Other suitable substrates will be well known to those skilled in the art, for example PVC, poly (ether sulphone) (PES), poly (ether ether ketone) (PEEK), and polycarbonate.

The enzyme may be any suitable oxidoreductase enzyme; for example glucose oxidase, cholesterol oxidase, or lactate oxidase.

Other aspects and benefits of the invention will appear in the following specification, drawings and claims.

BRIEF DESCRIPTION OF THE DRAWINGS

The invention will now be further described, by way of example, with reference to the following drawings in which.

DETAILED DESCRIPTION

Preparation Of BSA-Pt/Carbon

Figure 1:
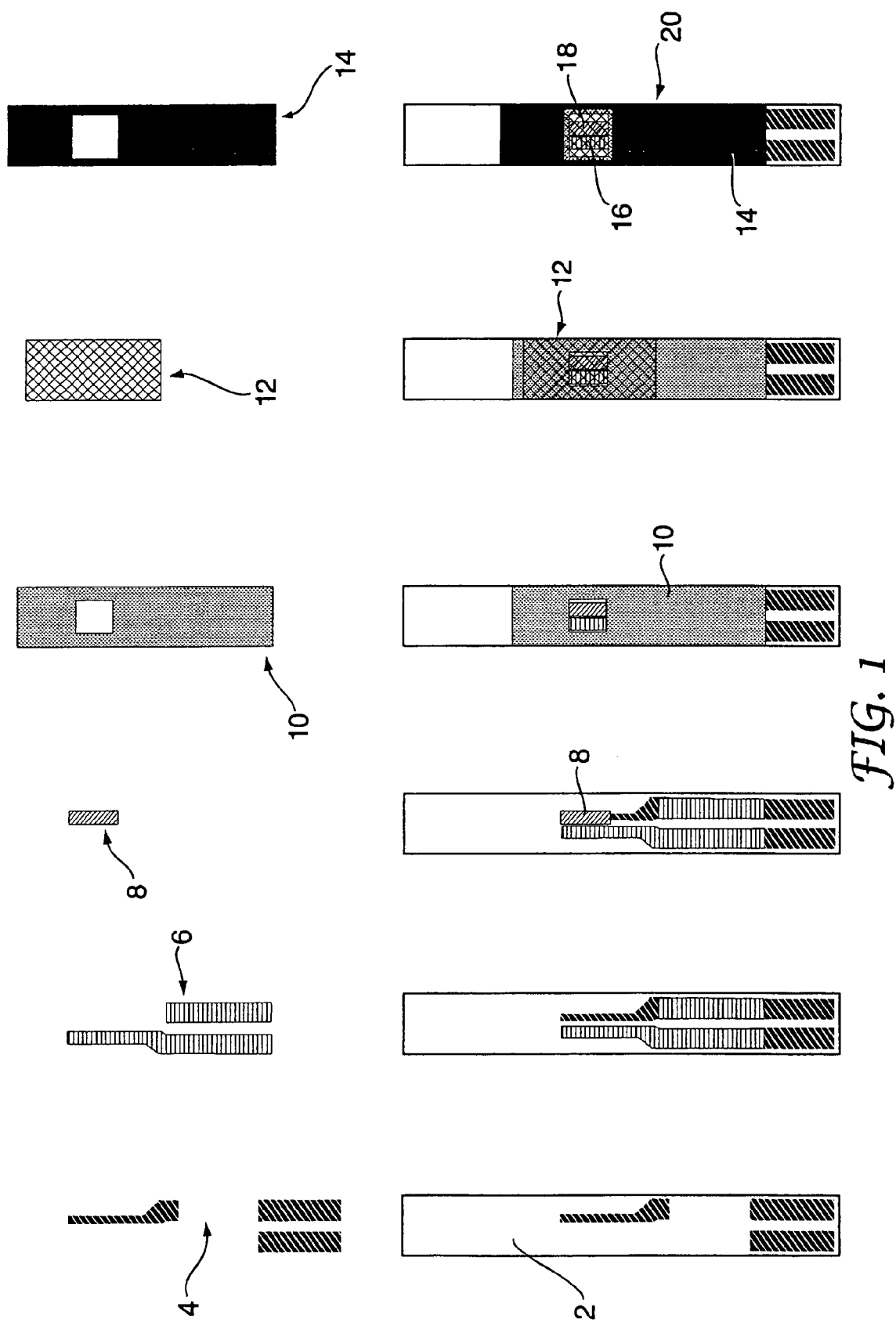
FIG. 1 shows stages in the formation of a biosensor in accordance with an aspect of the invention.

In a 250 mL glass bottle, 6.4 g of BSA, Miles Inc. was dissolved in 80 mL of phosphate buffered saline (PBS) and 20 g of 10% Pt/XC72R carbon, MCA Ltd, was gradually added with constant stirring. The bottle was then placed on a roller mixer and allowed to incubate for two hours at room temperature.

A Buchner funnel was prepared with two pieces of filter paper, Whatman™ No 1. The mixture was poured into the funnel and the carbon washed three times with approximately 100 mL of PBS. The vacuum was allowed to pull through the cake of carbon for about 5 minutes to extract as much liquid as possible. The cake of carbon was carefully scraped out into a plastic container and broken up with a spatula. The carbon was then placed in an oven at 30° C. overnight to dry. The purpose of this procedure is to block active sites on the carbon hence to aid the shelf stability and reproducibility of the carbon's properties.

Preparation of Platinum Group Metal/Carbon Inks

BSA-Pt/Carbon was prepared in Metech 8101 polyester resin as the polymer binder, Terpineol BP, from RC Treatt, as a flow agent and Butyl Cellosolve Acetate (BCA) as a solvent for the ink.

The formulation of a first ink consisted of:

Ink Formulation (I)

| | |
|---|---|
| Metech 8101 resin | 54.05% |
| BSA-Pt/Carbon | 27.09% |
| BCA | 12.57% |
| Terpineol BP | 6.29% |

The resin, solvent and flow agent were initially blended together prior to adding the carbon fraction. Initially the formulation was hand mixed followed by several passes through a triple roll mill. This produces a smooth homogeneous thixotropic carbon ink suitable for screen-printing.

An alternative formulation is one similar to that described in U.S. Pat. No. 4,970,145, the content of which is incorporated herein by reference, in which glucose oxidase (GOD) is adsorbed onto the Pt/Carbon prior to BSA adsorption and incorporation into an ink.

In another formulation the level of BSA-Pt/carbon was reduced and graphite was added. The flow control agent was omitted and a surfactant was incorporated.

Ink Formulation (II)

| | |
|---|---|
| Metech 8101 resin | 45.32% |
| BSA-Pt/Carbon | 18.67% |
| graphite | 9.77% |
| BCA/cyclohexanone | 23.26% |
| Tween ® 20 | 2.98% |

Tween 20 is a surfactant supplied by Sigma-Aldrich. Tween is a registered trade mark of ICI Americas Inc. The solvent is a 50% v/v mixture of BCA and cyclohexanone. The additional volume of solvent compared to that used for Ink Formulation I was added to the ink after triple roll milling to bring the ink to a suitable viscosity for printing. The graphite was Timrex KS 15 (particle size <16 μm), from GS Inorganics, Evesham, Worcs. UK.

A further test formulation included GOD in the ink, as follows.

Ink Formulation (III)

| | |
|---|---|
| Metech 8101 resin | 44.68% |
| BSA-Pt/Carbon | 18.42% |
| graphite | 9.64% |
| BCA/cyclohexanone | 22.94% |
| Tween ® 20 | 2.94% |
| glucose oxidase | 1.38% |

Preparation of Drop Coating Solution

The coating solution is water-based and consists of a high concentration of buffer, preferably phosphate at pH 8. It has been found that buffering capacity is more important than ionic strength. In this example the solution contains glucose oxidase and a system stabiliser, in this example trehalose.

| Buffer | $KH_2PO_4/K_2HPO_4$ | 385 mM, pH 8 | Sigma |
|---|---|---|---|
| Enzyme | Glucose oxidase | 4080 U/mL | Biozyme |
| Stabiliser | Trehalose | 1% | Sigma |

Preferred Ranges

| Buffer | 300–1000 mM, pH 7–10 |
|---|---|
| Enzyme | 500–12000 U/mL (1.85–44.4 mg/mL) |
| Stabiliser | 0.5–10% |

The activity of the glucose oxidase is about 270 units per milligram of material (360 units/mg of protein because the enzyme comes in a preparation with other lyophilisation and stabilisation agents).

If the enzyme is located in the base layer, for example in a base layer prepared using Ink Formulation III, the drop coating solution may contain only buffer, optionally with the stabiliser.

Method of Manufacture

Glucose test strips (biosensors) were manufactured using a combination of screen printing and drop coating technologies.

Other printing and/or coating technologies, well known per se to those skilled in the printing and coating arts may also be used.

With reference to FIG. 1, a base substrate 2 is formed from a polyester (Valox™). Conductive tracks 4 were printed onto the substrate 2 as a Conductive Carbon Paste, product code C80130D1, Gwent Electronic Materials, UK. The purpose of this ink is to provide a conductive track between the meter interface and the reference and working electrodes. After printing, this ink was dried for 1 minute in a forced air drier at 130° C.; The second ink printed on top of the conductive carbon 4 is a Silver/Silver Chloride Polymer Paste, product code C61003D7, Gwent Electronic Materials, UK. This ink 6 is not printed over the contact area or the working area. This ink 6 forms the reference electrode 16 of the system. It is dried at 130° C. in a forced air drier for 1 minute.

The next layer is the platinum group metal carbon ink (Ink Formulations I, II or III) which is printed as a layer 8 onto the conductive carbon 4 in the target area. This ink is dried for 1 minute at 90° C. in a forced air drier to form a base layer about 12 μm thick. A first dielectric layer 10 is then printed. The first dielectric layer 10 is MV27, from Apollo, UK. The purpose of this layer is to define a target area for blood application and to insulate the system. It is dried at 90° C. for 1 minute in a forced air drier. A spreading layer 12, which consists of a surfactant-coated polyester mesh, Saaticare PES 105/52, Saati, Italy, or Petex 07-105/52, Sefar, Switzerland, is then placed over the target area. This is then sealed onto the electrode using a further layer 14 of MV27 dielectric; and dried. If desired, the base layer 8 can alternatively be printed after the first dielectric layer 10. However, it is preferred to print the base layer 8 first, since the subsequent application of the first dielectric layer 10 removes some of the tolerance requirements of the print.

The drop coat layer is then applied to the electrode using BioDot drop coating apparatus. The volume of drop coating solution used is 1 μl; this is dried in a forced air drier for 1 minute at 50° C. The final biosensor 20 has a reference electrode 16 and a working electrode 18 within the target area. The working electrode comprises the base layer 8 on a conductive carbon layer 4 on the base substrate 2, and a top layer including the buffer. The mesh 12 helps to spread out a sample of blood when this is applied to the target area.

Preparation of Comparative Biosensor (Prior Art)

An ink was formulated as described above (Ink Formulation I) but using glucose oxidase (GOD) in place of BSA. The ink was used in the manufacture of a biosensor as described above (Method of Manufacture) but without the drop coating step.

Standard Test Procedures

The test procedure involves connecting the test strips to a potentiostat. A potential of 350 mV is applied across the working and reference electrodes after application of a sample, in this example a sample of whole blood (WB). The potential is maintained for 15 seconds, after which the current is measured; this current is used to prepare response graphs. Results for graphs 2 to 10 were obtained using Ink Formulation I.

Explanation of Figures

Figure 2:
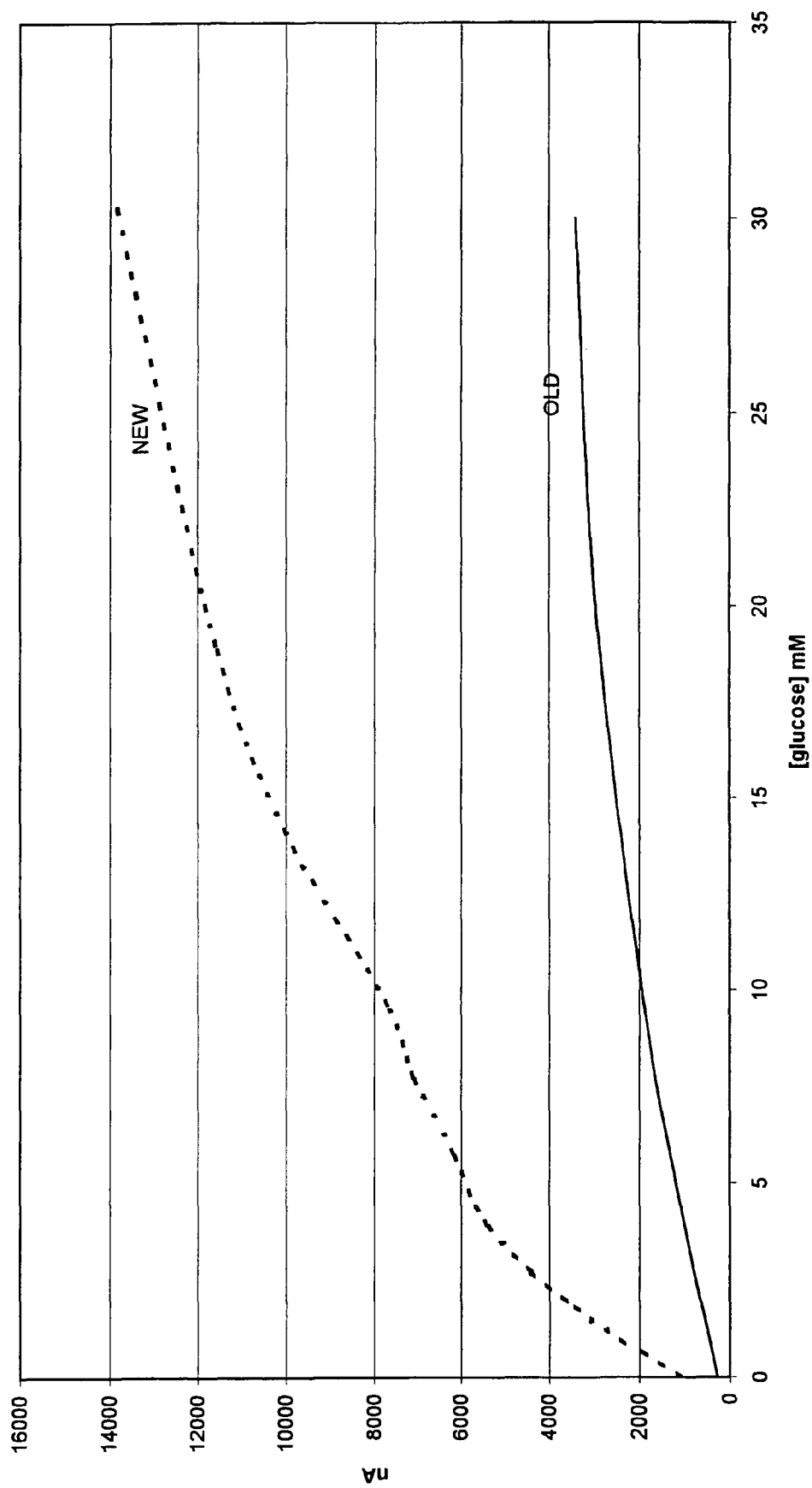
FIG. 2 is a graph illustrating a comparison between glucose calibrations on a biosensor of the present invention and a prior art biosensor.

Comparison between glucose calibrations on old and new methodologies (FIG. 2). The old methodology refers to the prior art non-mediated Comparative Biosensor, which does not include high buffer concentrations. It can be seen that increasing the pH from pH 7.4 within the ink at low buffer concentrations to pH 8 at a high local buffer concentration with a top layer which also includes the enzyme results in a dramatic increase in sensitivity.

Figure 3:
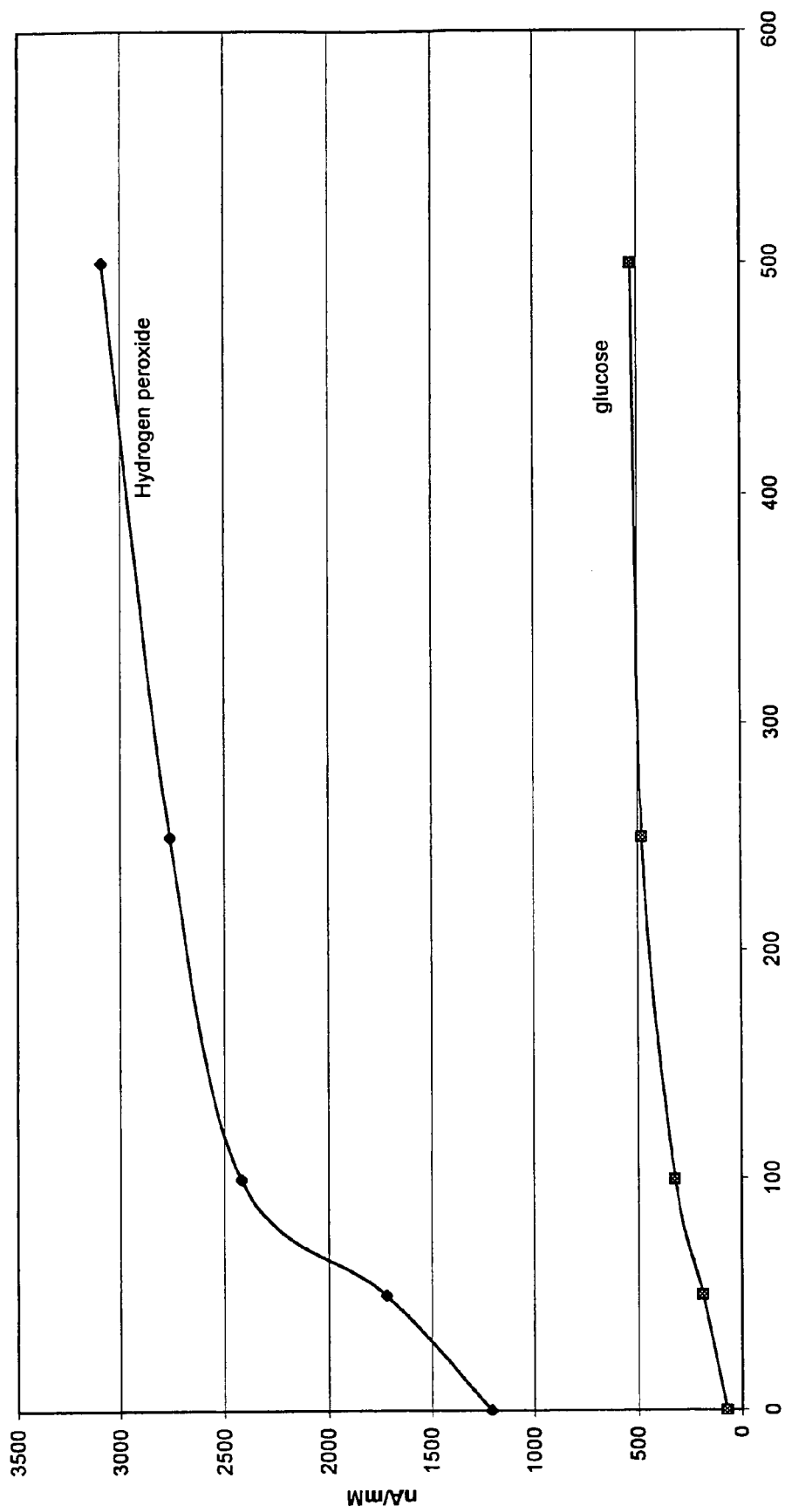
FIG. 3 is a graph illustrating the effect of phosphate buffer in the top layer on response.

Effect of Phosphate buffer concentration, in top layer, on response (FIG. 3). It can be seen in this plot that the sensitivity of the response to glucose and also to hydrogen peroxide is dramatically increased by the concentration of phosphate buffer. The buffer pH was pH 7.4. This plot also demonstrates the efficiency gap between hydrogen peroxide measurement and glucose measurement. Hydrogen peroxide is being directly oxidised at the platinum surface whereas glucose has to react with glucose oxidase and produce hydrogen peroxide. Where glucose oxidase is in the top layer it rapidly comes into solution on application of sample diffusing into the bulk. Hydrogen peroxide produced by glucose oxidation has a variable diffusion distance to the electrode surface whereas hydrogen peroxide applied in the sample does not. The ideal situation would be to have glucose oxidase immobilised at the electrode surface yet have high ionic strength and stabilisers in the top layer.

Figure 4:
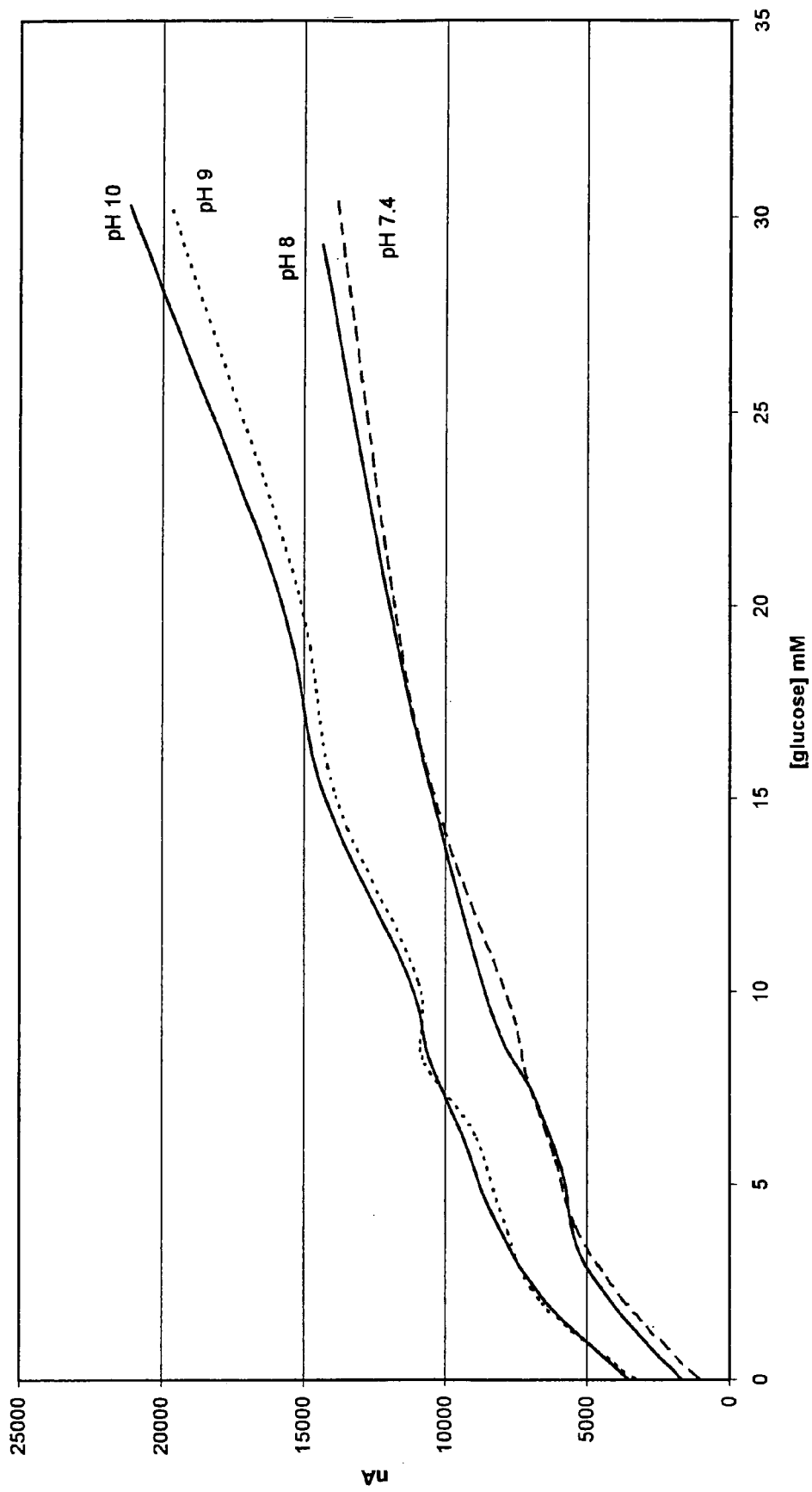
FIG. 4 is a graph illustrating the effect of pH on glucose response.

Effect of pH on glucose response (FIG. 4). This plot shows that the glucose response is increased with pH. The buffer concentration at each pH is maintained at 350 mM. This cannot be due to increased activity from the glucose oxidase as it has its pH maximum at pH 5.6; at pH 10 the glucose oxidase should be grossly inhibited. A possible mechanism for the increased glucose related response is that the glucose is being directly oxidised at the electrode surface. It is known that glucose will oxidise at a platinum surface but under normal conditions this response should be very small in comparison with the enzyme facilitated glucose oxidation. It may be that high buffer concentration coupled with high pH results in a huge enhancement in the direct oxidation of glucose, although this is unlikely. Alternatively if the hydrogen peroxide response were to increase with pH this might compensate for some of the drop-off in glucose oxidase response.

Figure 5:
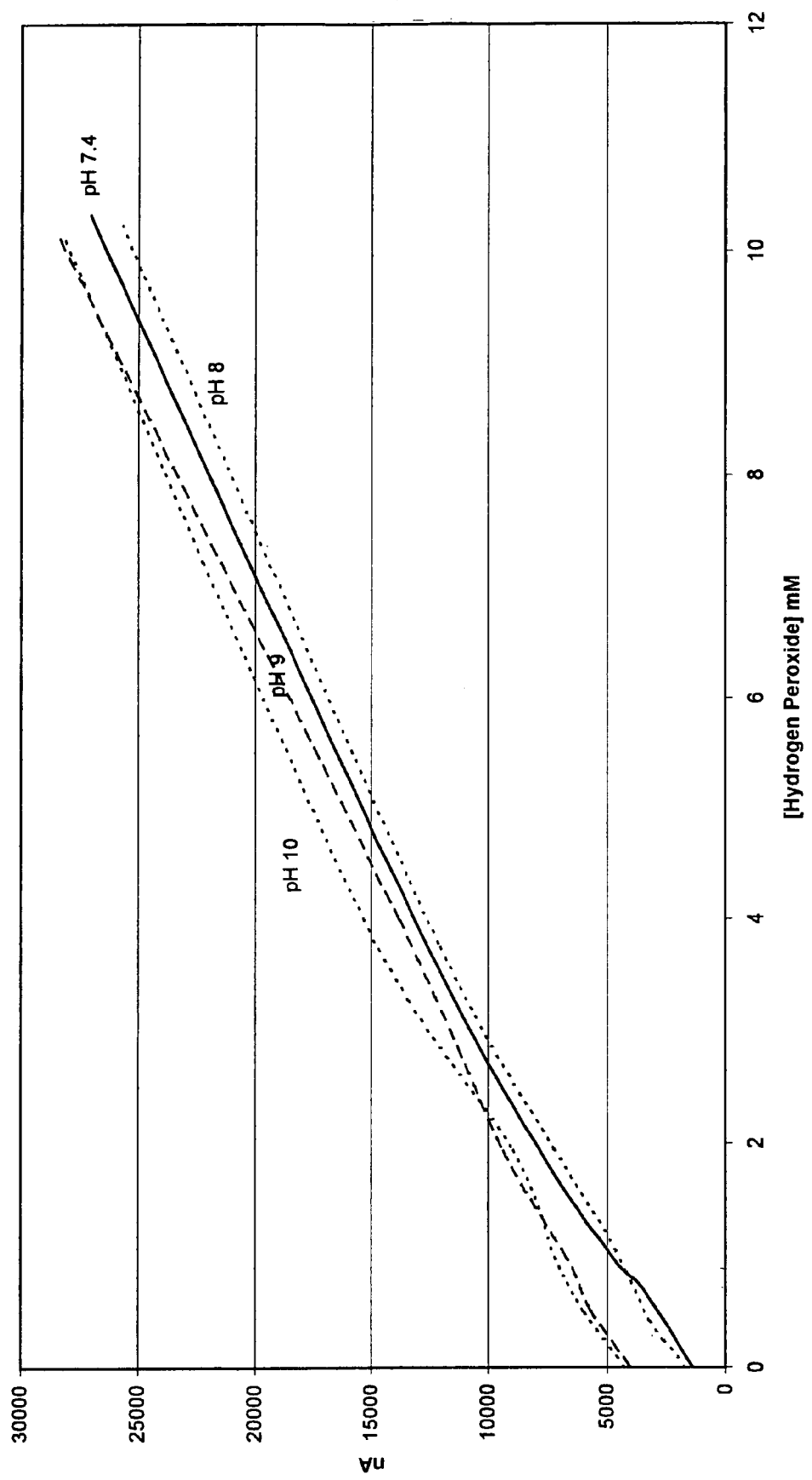
FIGS. 5 and 6 are graphs illustrating the effect of pH on hydrogen peroxide response.
Figure 6:
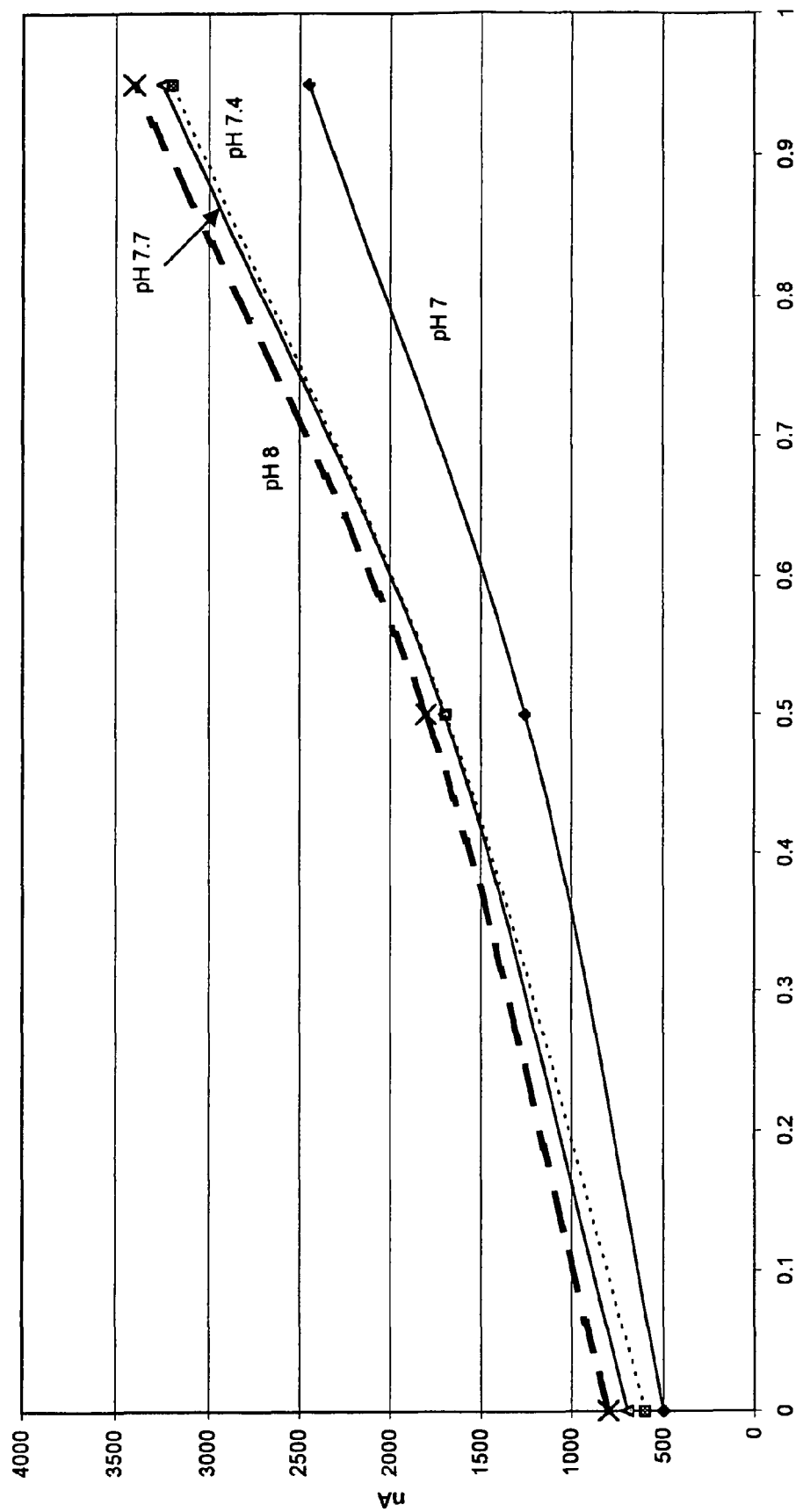

Effect of pH on hydrogen peroxide response (FIG. 5, FIG. 6). This plot shows very little change in hydrogen peroxide response with pH, except at low hydrogen peroxide concentrations. The sensitivity to hydrogen peroxide is a factor of five higher than that to glucose hence it is more applicable to look at low hydrogen peroxide concentrations. Increased pH will result in ionisation of active groups on the carbon surface, this increases the non-Faradaic component of the electrochemical response resulting in an increased intercept.

Figure 7:
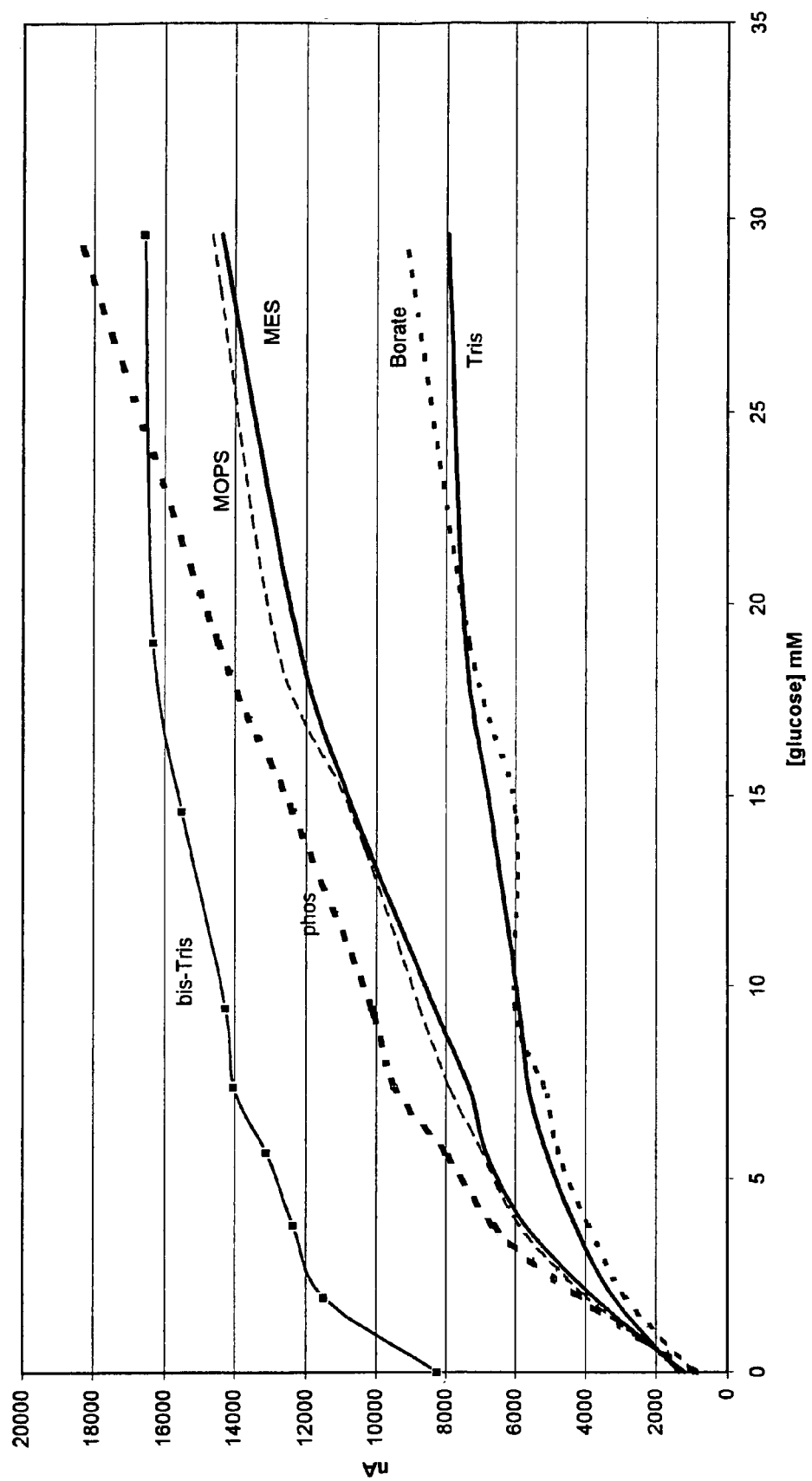
FIGS. 7 and 8 are graphs illustrating the effect of pH on glucose response.
Figure 8:
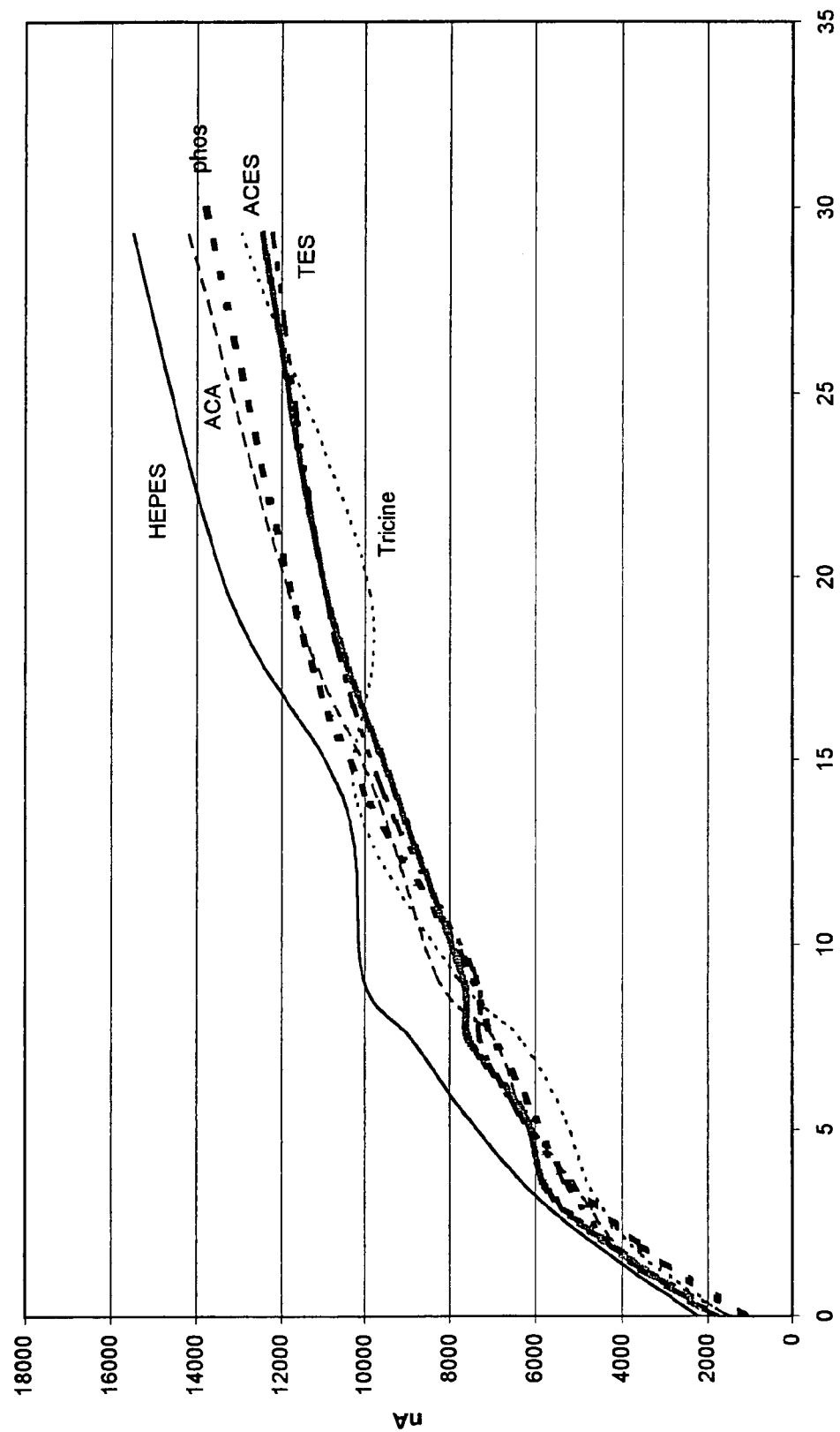

Effect of buffer type on glucose response (FIG. 7, FIG. 8). Different buffers were evaluated. All buffers were drop coated on the electrode surface and dried. All buffers were at pH 7.4 and 350 mM. The buffers could be separated into three distinct groups.

group A—bis-tris—this buffer resulted in a high intercept and relatively poor sensitivity to glucose.

group B—phosphate, MOPS, MES, HEPES, ACA, ACES, TES and Tricine—these buffers all gave roughly similar responses, low intercepts and reasonable sensitivity to glucose.

group C—Borate, Tris—these buffers gave low intercepts but poor glucose sensitivity.

Figure 9:
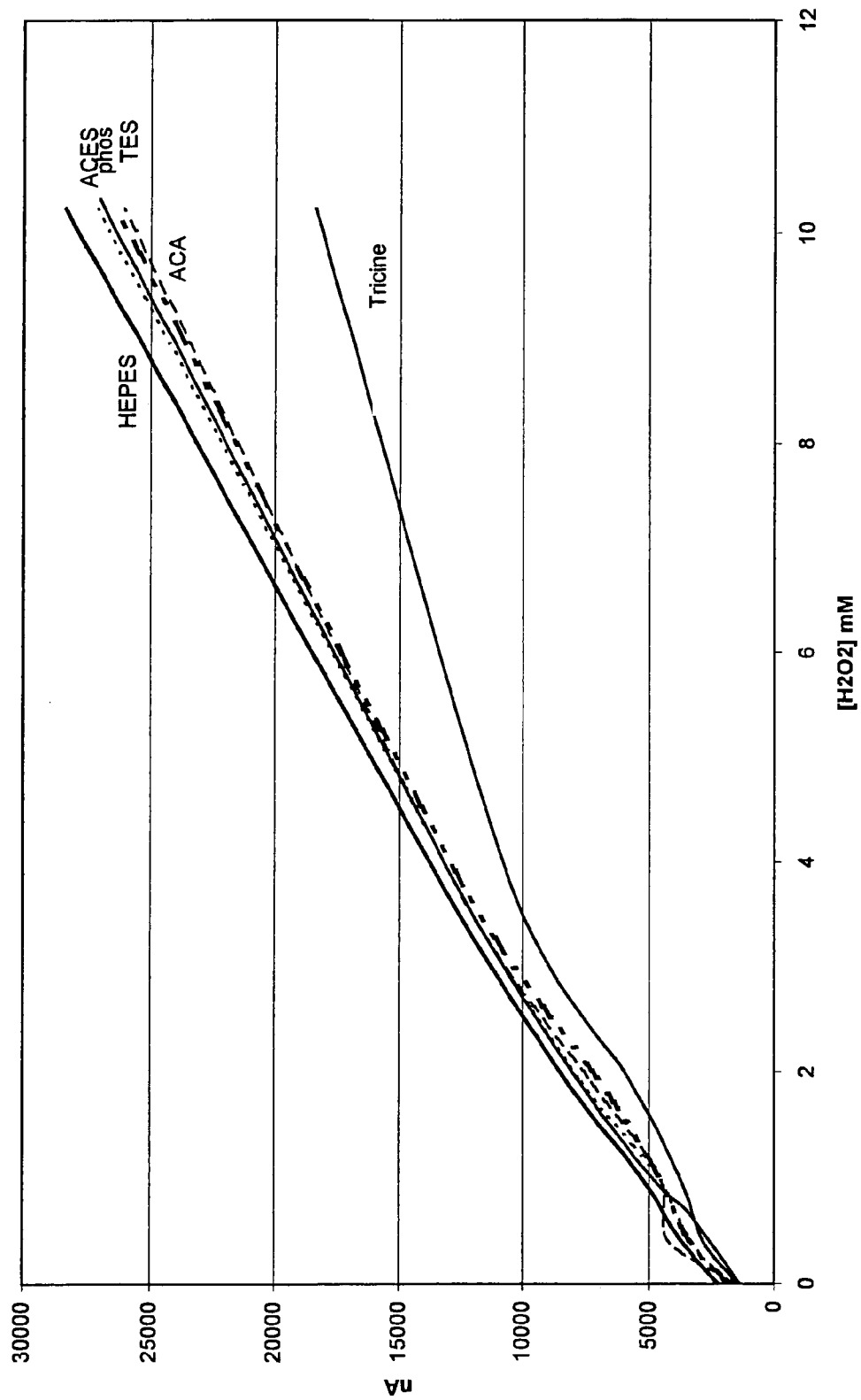
FIGS. 9 and 10 are graphs illustrating the effect of buffer type on hydrogen peroxide response.
Figure 10:
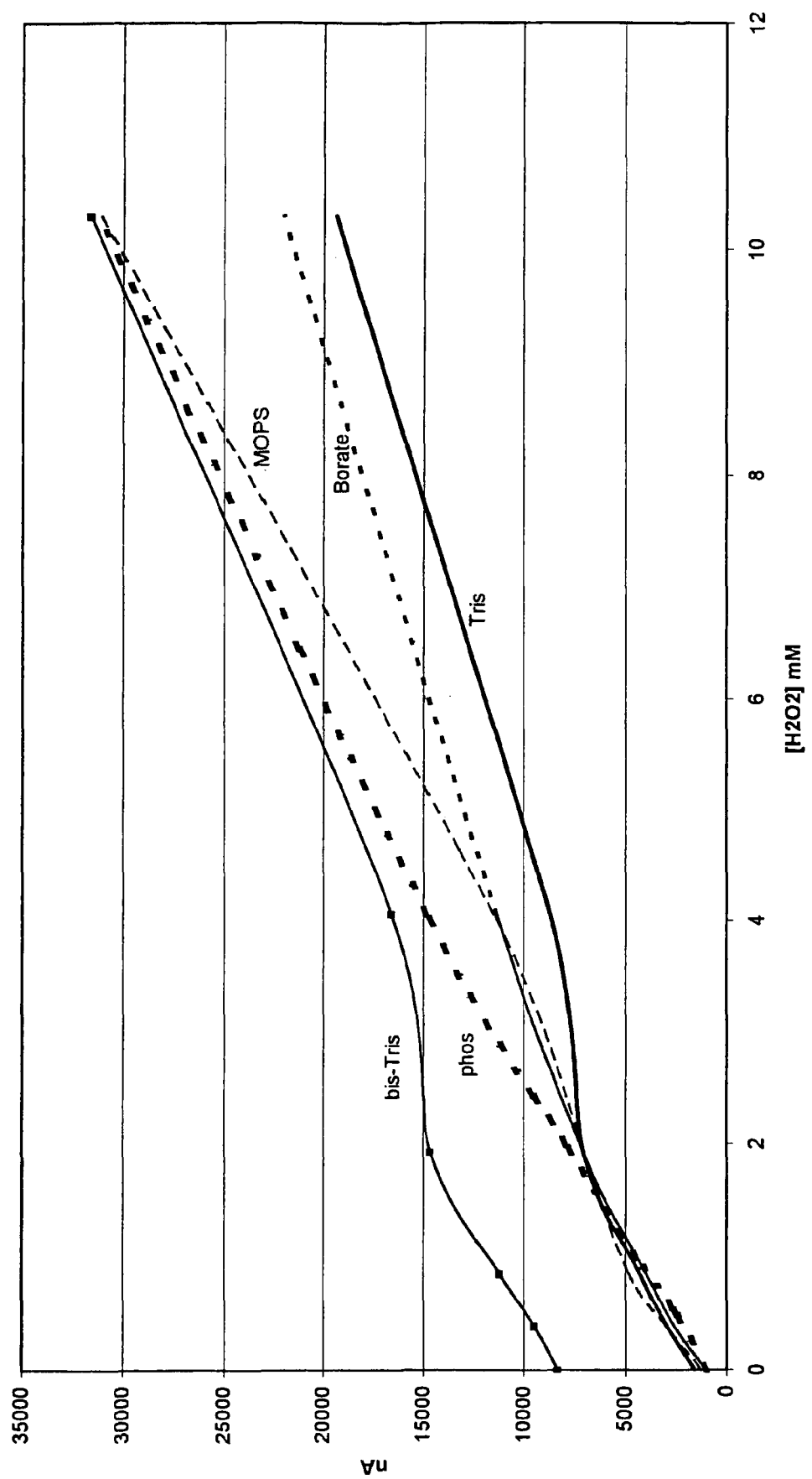

Effect of buffer type on hydrogen peroxide response (FIG. 9, FIG. 10). Similar electrodes to that used for the effect of buffer type on glucose response were used in this experiment. The buffer types could be separated into 3 groups.

group A—bis-tris—this buffer resulted in a high intercept but reasonable sensitivity above 4 mM.

group B—phosphate, MOPS, HEPES, ACES, TES, ACA—all gave similar responses low intercept and reasonable sensitivity to hydrogen peroxide.

group C—Borate, Tris and Tricine—low intercepts and reduced sensitivity to hydrogen peroxide There are similar trends when comparing the glucose and hydrogen peroxide sensitivities with buffer type. This would imply that the major effect of the buffer is on hydrogen peroxide oxidation. The bis-tris buffer is electrochemically active which results in the high background current at zero hydrogen peroxide. The Borate Tris and Tricine buffers have pKa values greater than 8, hence they would have poor buffering capacity at pH 7.4. All the other buffers have pKa values close to 7.4.

Turning now to FIGS. 11 to 18, these show results for biosensors in which the base layer is printed using Ink Formulation II with various drop coat formulations to provide the top layer, except where otherwise stated.

The concentration of buffer in the drop coat formulation is expressed as mmol $L^{-1}$ (mM), and the concentration of GOD enzyme is expressed as mg/mL. Each drop coat solution also contained 1% of trehalose.

Figure 11:
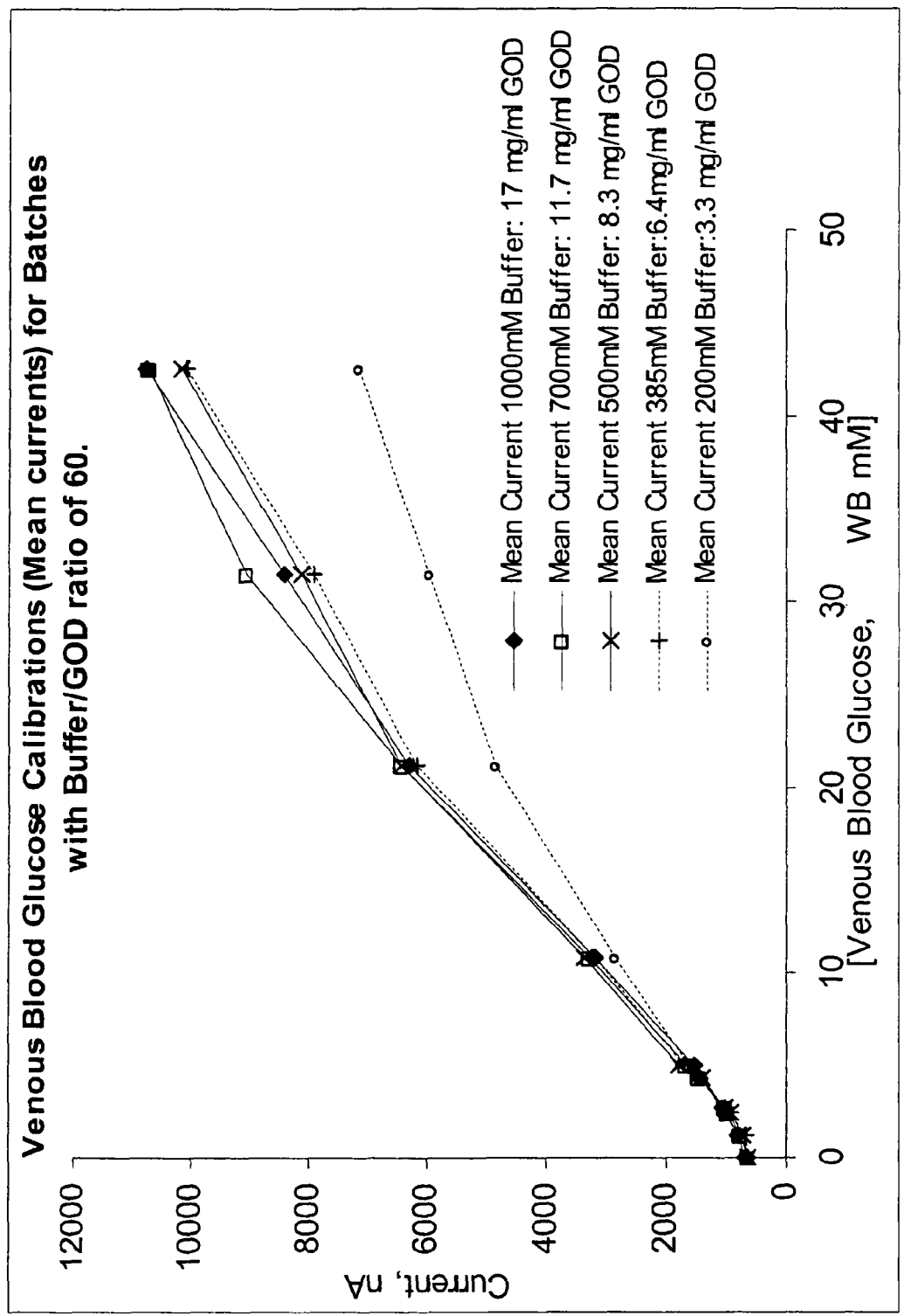
FIG. 11 shows calibration graphs for biosensors with a fixed buffer/enzyme ratio.

FIG. 11 shows venous blood glucose calibrations for batches with phosphate buffer/GOD ratios (mol/kg) of about 60. The results show that for a fixed buffer/enzyme ratio above a threshold concentration the product gives substantially the same response. A preferred minimum buffer concentration is about 300 mM.

Figure 12:
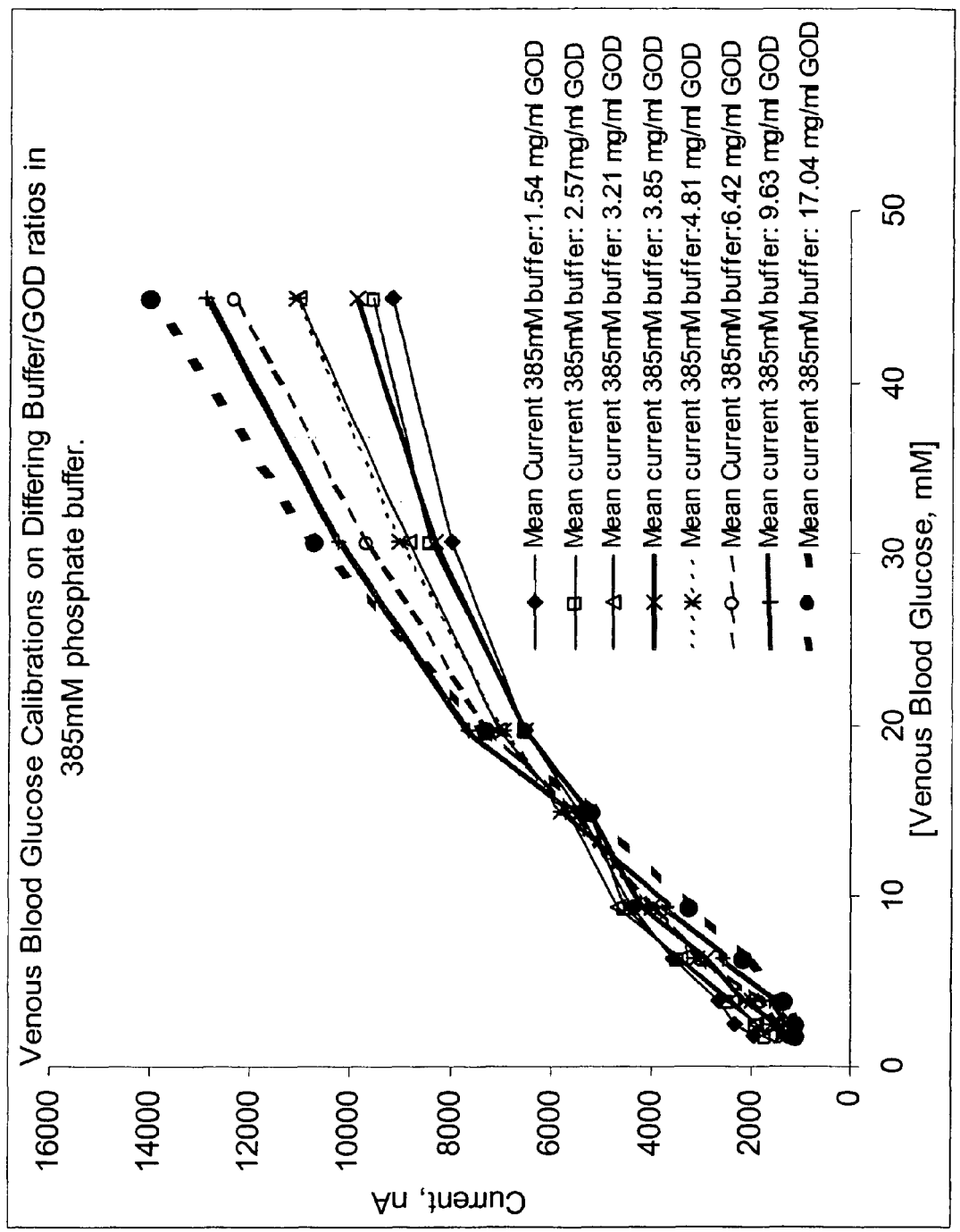
FIGS. 12 and 13 show calibration results for biosensors with different buffer/enzyme ratios.
Figure 13:
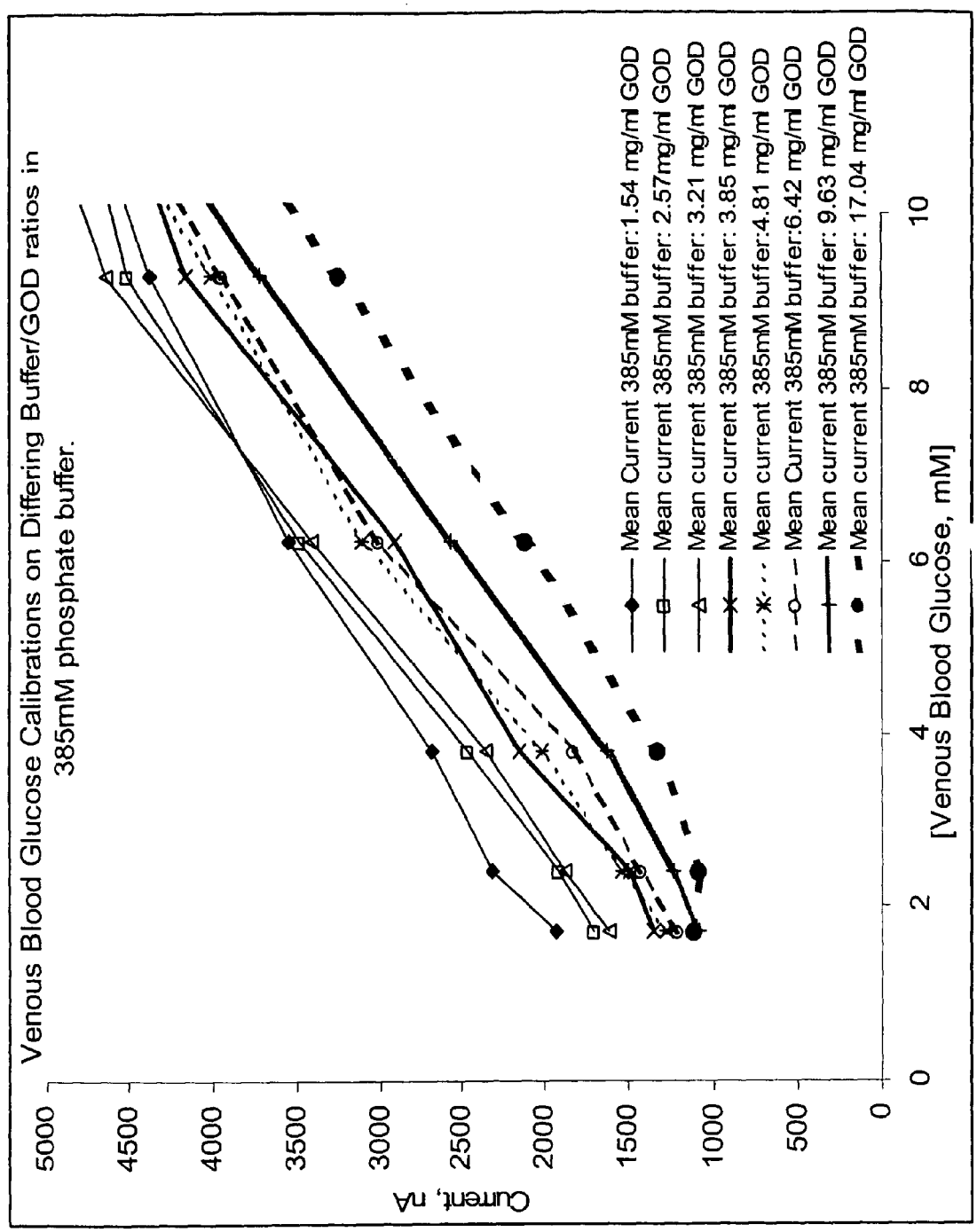

FIG. 12 shows blood glucose calibration of biosensors made with formulations of differing GOD concentrations and a fixed phosphate buffer concentration of 385 mM. FIG. 13 is part of the graph of FIG. 12, expanded to show low glucose concentration results more clearly. The graphs illustrate that increasing the ratio of buffer to enzyme (decreasing enzyme) improves sensitivity at critical low blood glucose concentrations. Above the minimum threshold, adjustment of the ratio of buffer to enzyme can be used to "tune" the profile of the response to the biosensor to blood glucose. To obtain better linearity of response a preferred buffer/enzyme ratio (mol/kg) is in the range 30-80, notably 40-60.

Figure 14:
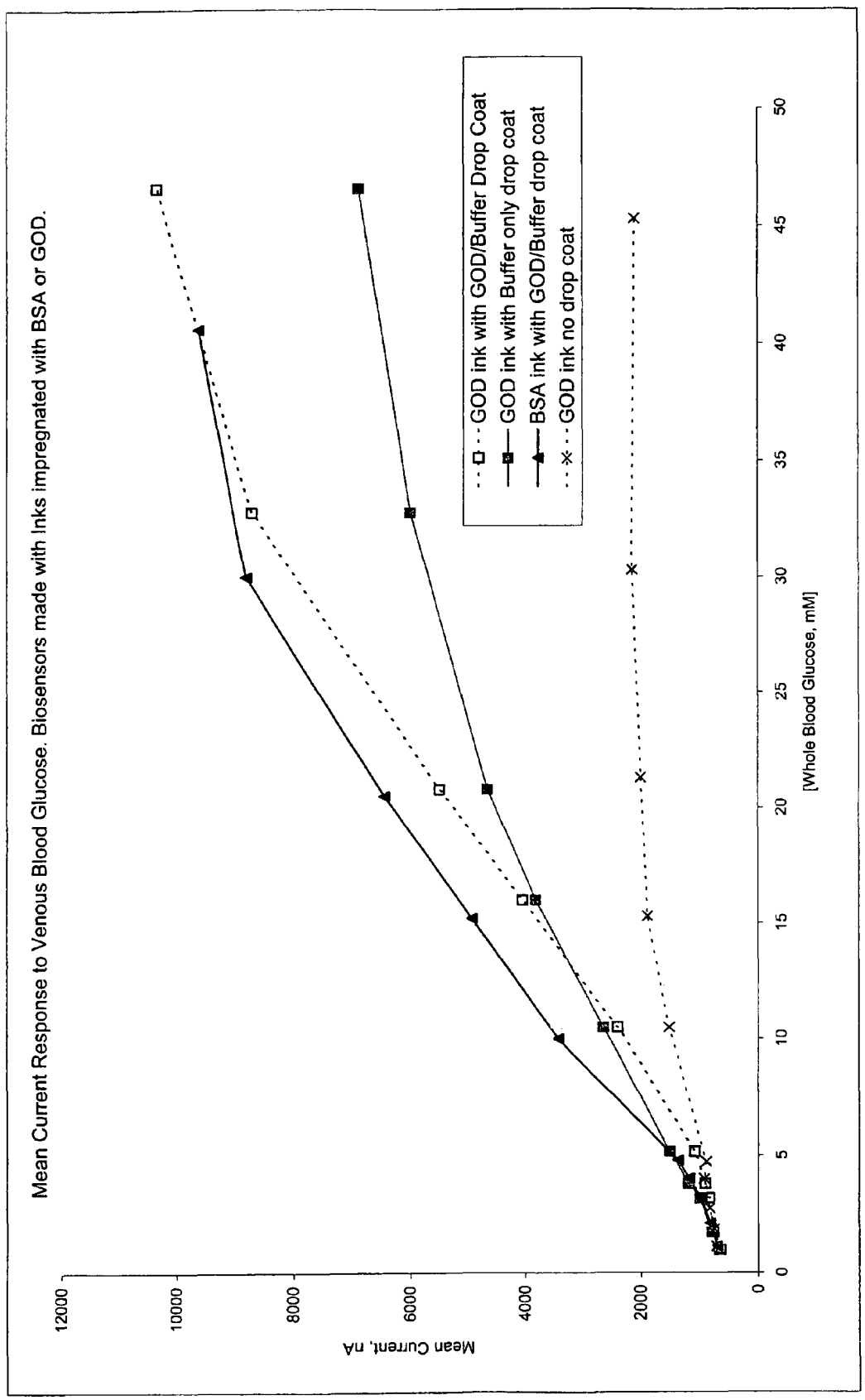
FIG. 14 shows results for different combinations of ink and drop coats.

Referring now to FIG. 14, results are shown for different ink and drop coat formulations. The results labelled BSA ink are for a base coat ink made up in accordance with Ink Formulation II. The results labelled GOD ink are for a base coat ink made up in accordance with Ink Formulation III. Results are shown for drop coat solutions made in accordance with the formulation given earlier, and also for a similar solution without GOD, and for a case where no drop coat was applied. In the latter case there is little sensitivity, but in the other cases glucose levels can be measured at all practical concentrations. Best results are obtained when both enzyme and buffer are present in the top coat.

Figure 15:
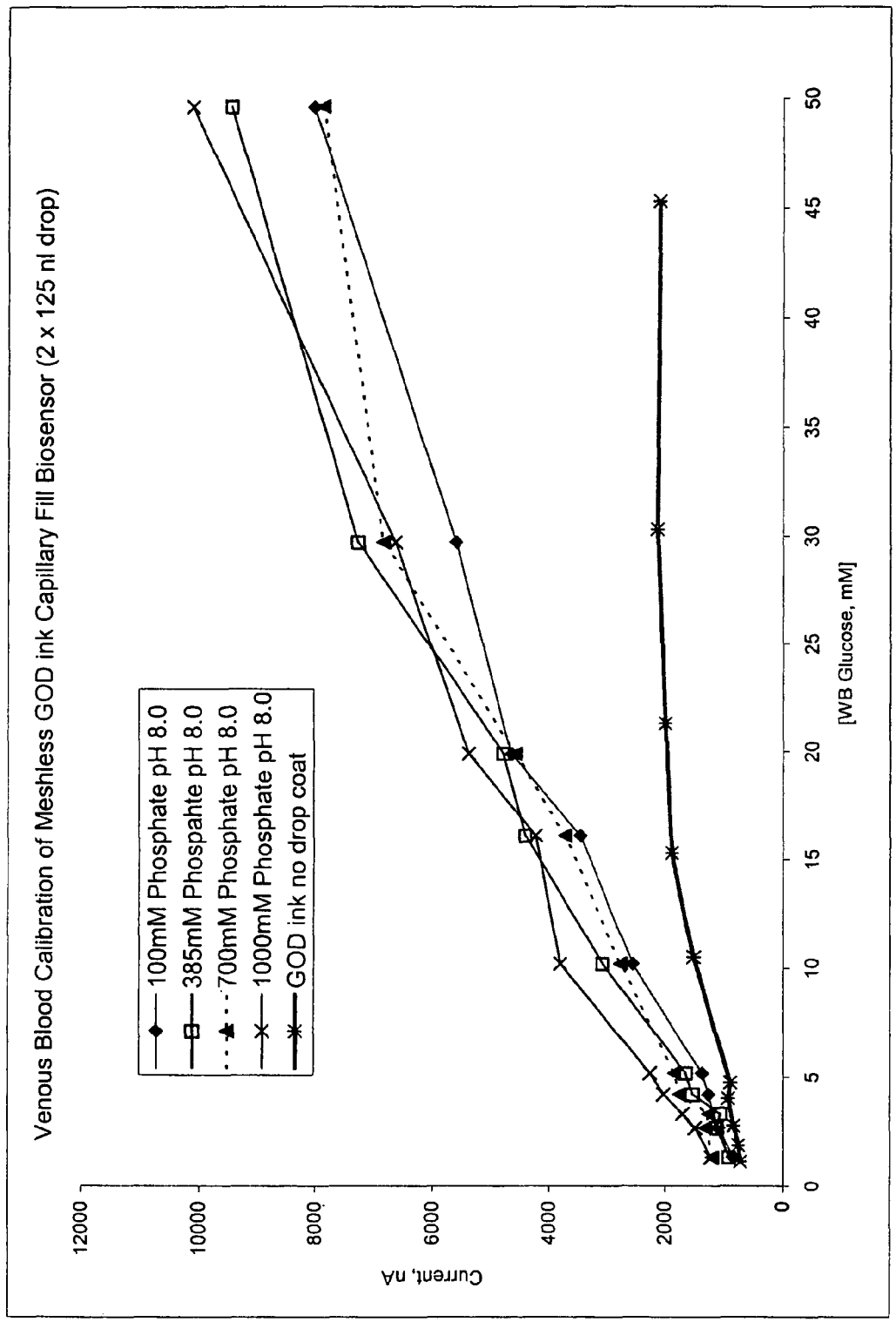
FIGS. 15 and 16 are graphs of results for biosensors without a mesh layer.
Figure 16:
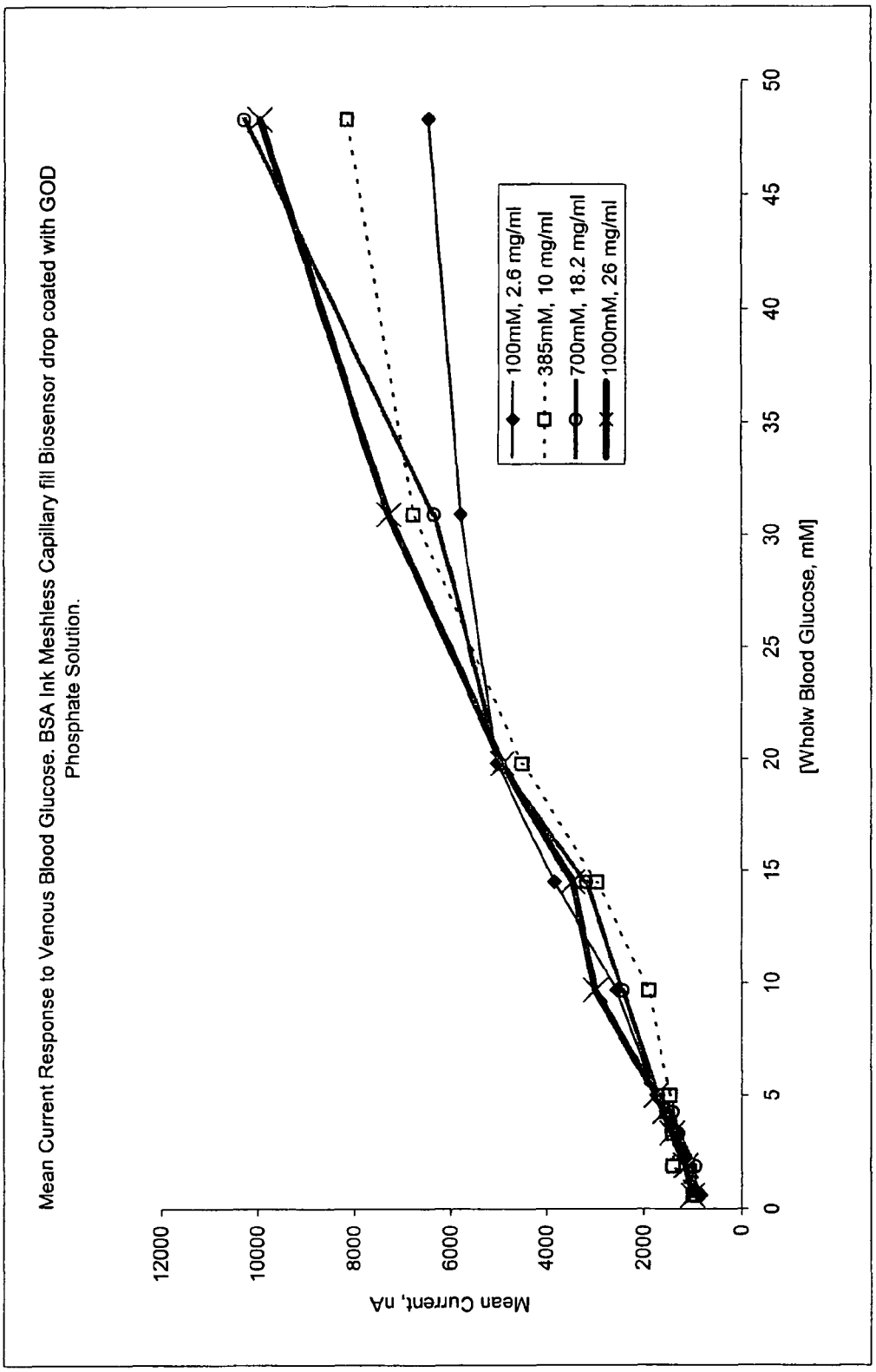

Calibration graphs are shown in FIG. 15, for a biosensor without the mesh layer 12. Omission of the mesh layer 12 permits lower drop coat volumes to be used, because applied fluid does not get drawn away from the working area by the mesh, but the drop application must be more precise. Results are shown for 2×125nL drops of phosphate in the drop coat solution, with base layers formed using the GOD ink (Ink Formulation III). Higher levels of buffer give better linearity. The graphs in FIG. 16 show results for biosensors having base layers formed using Ink Formulation II, and top layers formed using drop coat solutions with GOD and buffer. Here also, higher levels of buffer give better linearity.

Figure 17:
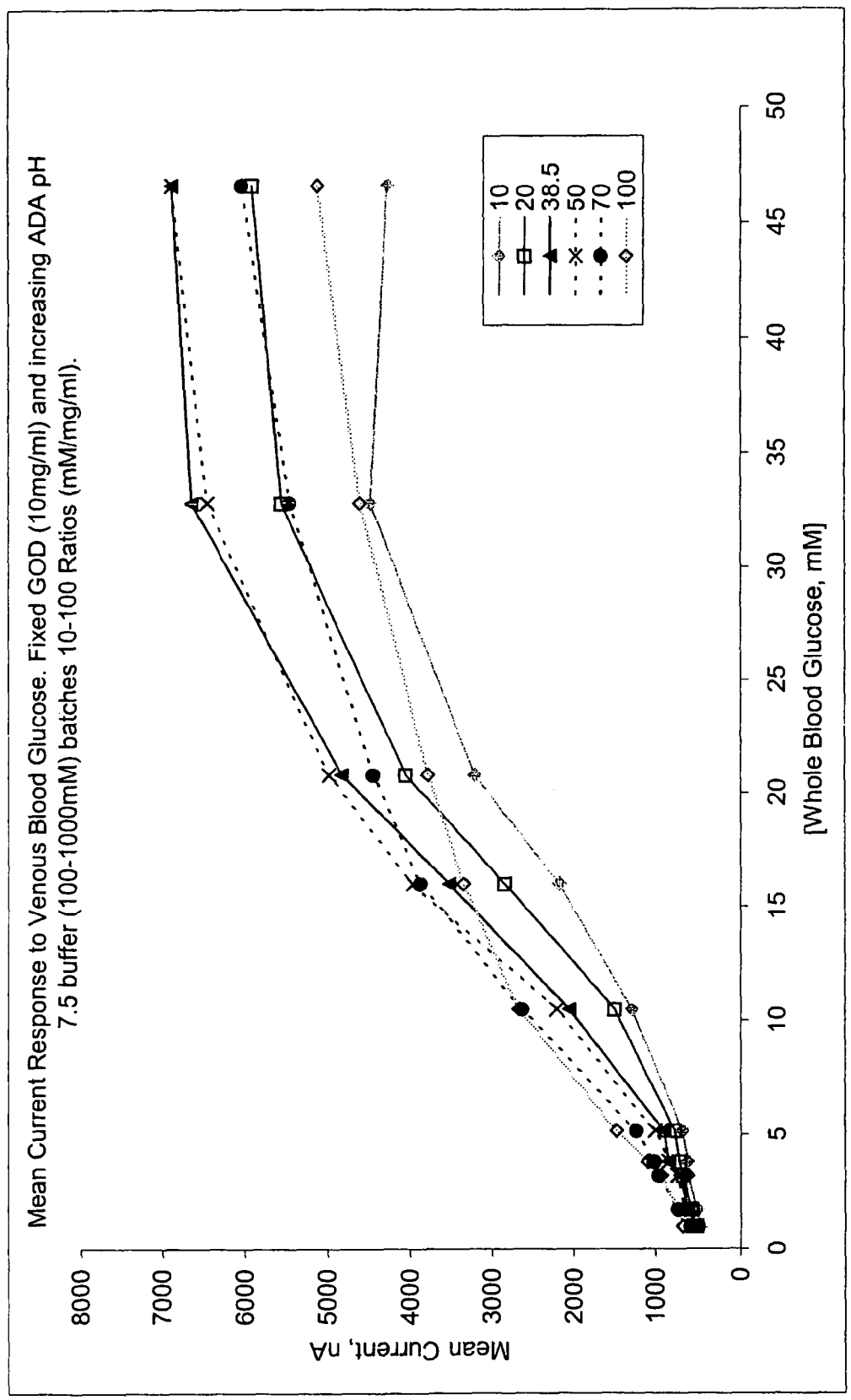
FIGS. 17 and 18 are graphs illustrating the effect of ADA buffer in the top layer on response.
Figure 18:
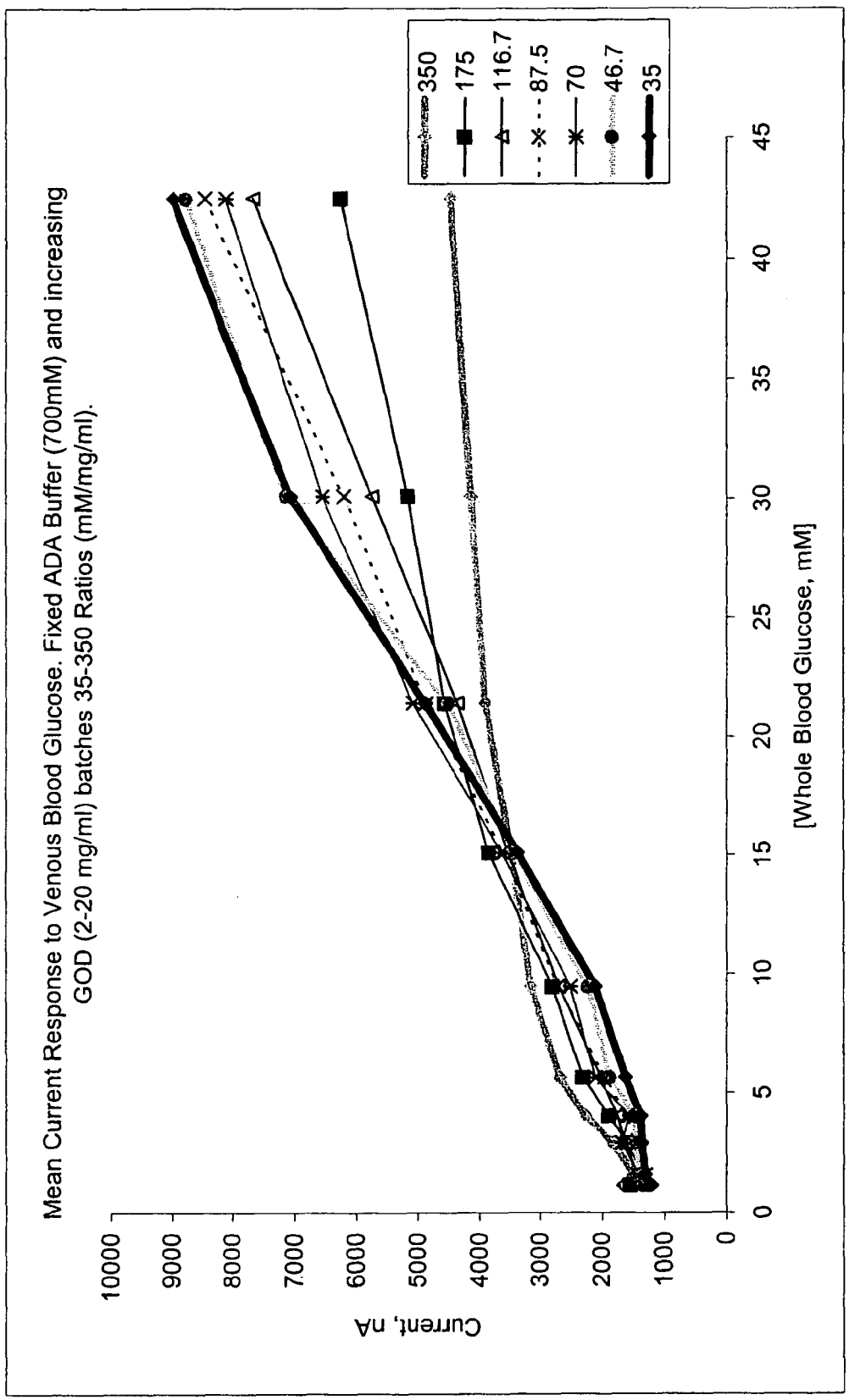

FIGS. 17 and 18 graph results for drop coat solutions of GOD and ADA buffer (N-(2-acetamido-2-iminodiacetic acid). The threshold buffer concentration is about 200 mM, and the preferred ratio (mol/kg) buffer/GOD is about 40-100, notably about 60-80.

The invention claimed is:

1. A non-mediated enzyme electrode for indicating amperometrically the catalytic activity of an oxidoreductase enzyme in the presence of a fluid containing a substance acted upon by said enzyme and of an electric potential on the electrode, said electrode comprising a base substrate on which is provided:
   (a) an electrically conductive base layer comprising finely divided platinum group metal or oxide bonded together by a resin;
   (b) a top layer printed or coated on the base layer, said top layer comprising a buffer and being soluble in said fluid; and
   (c) a catalytically active quantity of said oxidoreductase enzyme in at least one of said base layer and said top layer.

2. An enzyme electrode according to claim 1, wherein the buffer is selected from a group comprising: phosphate, ADA, MOPS, MES, HEPES, ACA, and ACES, or buffers with a pKa 7.4±1.

3. An enzyme electrode according to claim 1, wherein the buffer has a pH in the range 7 to 10.

4. An enzyme electrode according to claim 3, wherein the buffer has a pH in the range 7 to 8.5.

5. An enzyme electrode according to claim 1, further including a system stabiliser in the top layer, comprising a polyol which is not acted upon by the enzyme.

6. An enzyme electrode according to claim 5, wherein the system stabiliser is trehalose.

7. An enzyme electrode according to claim 1, wherein the oxidoreductase enzyme is glucose oxidase.

8. An enzyme electrode according to claim 1, wherein the base layer also contains particles of finely-divided carbon or graphite.

9. An enzyme electrode according to claim 8, wherein said finely divided particles of platinum group metal or oxide are adsorbed onto the surface of the finely-divided carbon or graphite.

10. An enzyme electrode according to claim 8, wherein the particles of finely divided carbon or graphite comprise carbon, and wherein the base layer further includes a blocking agent for blocking active sites of the carbon particles.

11. An enzyme electrode according to claim 10, wherein the said blocking agent comprises a protein or a polyol.

12. An enzyme electrode according to claim 11, wherein the blocking agent is bovine serum albumin (BSA) or trehalose.

13. An enzyme electrode according to claim 1, wherein the said oxidoreductase enzyme is located substantially in the said top layer.

14. An enzyme electrode according to claim 1, further including a spreading layer for aiding spreading of the said fluid.

15. An enzyme electrode according to claim 1, wherein the ratio of buffer to enzyme is in the range 30-80 mol/kg.

16. An enzyme electrode according to claim 15, wherein the ratio of buffer to enzyme is in the range 40-60 mol/kg.

17. A non-mediated biosensor for indicating amperometrically the catalytic activity of an oxidoreductase enzyme in the presence of a fluid containing a substance acted upon by said enzyme, the biosensor comprising:
  (a) a base substrate;
  (b) a working electrode and a reference electrode on the base substrate;
  (c) conductive tracks connected to the said electrodes for making electrical connections with a test meter apparatus;
wherein the working electrode includes:
  (d) an electrically conductive base layer comprising finely divided platinum group metal or oxide bonded together by a resin;
  (e) a top layer printed or coated on the base layer, said top layer comprising a buffer and being soluble in said fluid; and
  (f) a catalytically active quantity of said oxidoreductase enzyme in at least one of said base layer and said top layer.

18. A biosensor according to claim 17, wherein the buffer is selected from a group comprising: phosphate, ADA, MOPS, MES, HEPES, ACA, and ACES.

19. A biosensor according to claim 17, wherein the buffer has a pH in the range 7 to 10.

20. A biosensor according to claim 19, wherein the buffer has a pH in the range 7 to 8.5.

21. A biosensor according to claim 17, further including a system stabiliser in the top layer, comprising a polyol which is not acted upon by the enzyme.

22. A biosensor according to claim 21, wherein the system stabiliser is trehalose.

23. A biosensor according to claim 17, wherein the ratio of buffer to enzyme is in the range 30-80 mol/kg.

24. A biosensor according to claim 23, wherein the ratio of buffer to enzyme is in the range 40-60 mol/kg.

25. A biosensor according to claim 17, wherein the base layer also contains particles of finely-divided carbon or graphite.

26. A biosensor according to claim 25, wherein said finely divided particles of platinum group metal or oxide are adsorbed onto the surface of the finely-divided carbon or graphite.

27. A method of manufacturing a non-mediated biosensor for indicating amperometrically the catalytic activity of an oxidoreductase enzyme in the presence of a fluid containing a substance acted upon by said enzyme, the method comprising the steps of:
  (a) taking a base substrate having a working electrode and a reference electrode thereon, and conductive tracks connected to the said working and reference electrodes for making electrical connections with a test meter apparatus;
  (b) printing on the said working electrode an ink containing finely divided platinum group metal or oxide and a resin binder;
  (c) causing or permitting the said printed ink to dry to form an electrically conductive base layer comprising the said platinum group metal or oxide bonded together by the resin; and
  (d) forming a top layer on the base layer by printing or coating the base layer with a coating medium comprising or containing a buffer, the top layer being soluble in said fluid; wherein
  (e) a catalytically active quantity of said oxidoreductase enzyme is provided in at least one of said printed ink and said coating medium.

28. A method according to claim 27, wherein the coating medium is a coating fluid containing the buffer and wherein the method further comprises causing or permitting said coating fluid to dry to form a top layer on the base layer.

29. A method according to claim 28, wherein the coating fluid is applied by drop coating.

30. A method according to claim 28, further including the step of applying a spreading layer on the base layer prior to application of the coating fluid.

31. A method according to claim 30, wherein the step of applying a spreading layer comprises applying a surfactant-coated polyester mesh on the base layer.

32. A method according to claim 30, further comprising the step of applying a first dielectric layer prior to applying the spreading layer, the first dielectric layer being applied around the reference electrode and the working electrode to define a target area to which the said fluid containing a substance acted upon by the enzyme will be applied.

33. A method according to claim 32, further comprising the step of applying a second dielectric layer around the target area so as to secure the spreading layer in place.

34. A method according to 28, wherein said enzyme is provided in the coating fluid.

35. A method according to claim 28, wherein the concentration of buffer in the coating fluid is in the range 300 mmol/L to 1 mol/L.

36. A method according to claim 28, wherein the coating fluid has a pH in the range 7 to 8.5.

37. A method according to claim 27, wherein the ratio of buffer to enzyme is in the range 30-80 mol/kg.

38. A method according to claim 37, wherein the ratio of buffer to enzyme is in the range 40-60 mol/kg.

39. A method according to claim 27, wherein the buffer comprises phosphate or ADA.

40. A method according to claim 27, wherein said finely divided platinum group metal or oxide in said ink is adsorbed on the surface of particles of finely divided carbon or graphite.

41. A non-mediated enzyme electrode for indicating amperometrically the catalytic activity of glucose oxidase in the presence of glucose in whole blood and of an electric potential on the electrode, said electrode comprising a base substrate on which is provided:
  (a) an electrically conductive base layer comprising finely divided platinum group metal or oxide bonded together by a bonding agent;

(b) a top layer printed or coated on the base layer, said top layer comprising a buffer having a range from about pH 7 to about pH 8.5, and said top layer being soluble in whole blood; and (c) a catalytically active quantity of glucose oxidase in at least one of said base layer and said top layer.

42. A biosensor for indicating amperometrically the catalytic activity of glucose oxidase in the presence of glucose in whole blood, the biosensor comprising:

(a) a base substrate;

(b) a working electrode and a reference electrode on the base substrate;

(c) conductive tracks connected to the said electrodes for making electrical connections with a test meter apparatus;

wherein the working electrode comprises:

(d) an electrically conductive base layer comprising finely divided platinum group metal or oxide bonded together by a bonding agent;

(e) a top layer printed or coated on the base layer, said top layer comprising a buffer having a range from about pH 7 to about pH 8.5, and said top layer being soluble in said whole blood; and (f) a catalytically active quantity of said glucose oxidase in at least one of said base layer and said top layer.

43. A method of manufacturing a non-mediated biosensor for indicating amperometrically the catalytic activity of glucose oxidase in the presence of glucose in whole blood, the method comprising the steps of:

(a) taking a base substrate having a working electrode and a reference electrode thereon, and conductive tracks connected to the said working and reference electrodes for making electrical connections with a test meter apparatus;

(b) printing on the said working electrode an ink containing finely divided platinum group metal or oxide and a bonding agent;

(c) causing or permitting the said printed ink to dry to form an electrically conductive base layer comprising the said platinum group metal or oxide bonded together by the resin;

(d) forming a top layer on the base layer by printing or coating the base layer with a coating fluid containing a buffer and having a pH in the range about 7.0 to 8.5, said top layer being soluble in said whole blood; wherein (e) a catalytically active quantity of said glucose oxidase is provided in at least one of said printed ink and said coating fluid.

* * * * *